United States Patent
Daly

(10) Patent No.: US 9,737,470 B2
(45) Date of Patent: *Aug. 22, 2017

(54) SUNSCREEN COMPOSITIONS CONTAINING AN ULTRAVIOLET RADIATION-ABSORBING POLYMER

(71) Applicant: Johnson & Johnson Consumer Inc., Skillman, NJ (US)

(72) Inventor: Susan Daly, Basking Ridge, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/007,552

(22) Filed: Jan. 27, 2016

(65) Prior Publication Data

US 2016/0136073 A1    May 19, 2016

Related U.S. Application Data

(63) Continuation of application No. 13/926,248, filed on Jun. 25, 2013, now Pat. No. 9,248,092.

(60) Provisional application No. 61/665,464, filed on Jun. 28, 2012.

(51) Int. Cl.
| | |
|---|---|
| *A61K 8/86* | (2006.01) |
| *A61K 8/49* | (2006.01) |
| *A61Q 17/04* | (2006.01) |
| *A61Q 19/00* | (2006.01) |
| *A61K 8/06* | (2006.01) |
| *A61K 8/55* | (2006.01) |

(52) U.S. Cl.
CPC ............. *A61K 8/496* (2013.01); *A61K 8/062* (2013.01); *A61K 8/55* (2013.01); *A61K 8/86* (2013.01); *A61Q 17/04* (2013.01); *A61Q 19/00* (2013.01); *A61K 2800/26* (2013.01); *A61K 2800/30* (2013.01); *A61K 2800/49* (2013.01); *A61K 2800/596* (2013.01)

(58) Field of Classification Search
None
See application file for complete search history.

(56) References Cited

U.S. PATENT DOCUMENTS

| | | |
|---|---|---|
| 4,107,290 A | 8/1978 | Jacquet et al. |
| 4,322,522 A | 3/1982 | Johnson et al. |
| 4,399,297 A | 8/1983 | Thoemel et al. |
| 4,528,311 A | 7/1985 | Beard et al. |
| 4,839,160 A | 6/1989 | Forestier et al. |
| 4,897,259 A | 1/1990 | Murray et al. |
| 5,039,782 A | 8/1991 | Langer et al. |
| 5,138,089 A | 8/1992 | Sabatelli |
| 5,157,091 A | 10/1992 | Masataka et al. |
| 5,166,234 A | 11/1992 | Kawaguchi et al. |
| 5,250,652 A | 10/1993 | Langer et al. |
| 5,399,371 A | 3/1995 | Harris |
| 5,459,222 A | 10/1995 | Rodgers et al. |
| 5,487,885 A | 1/1996 | Sovak et al. |
| 5,585,090 A | 12/1996 | Yoshioka et al. |
| 5,741,924 A | 4/1998 | Sovak et al. |
| 5,843,410 A | 12/1998 | Kim et al. |
| 5,869,030 A | 2/1999 | Dumler et al. |
| 5,869,099 A | 2/1999 | Keller et al. |
| 6,001,337 A | 12/1999 | Keller et al. |
| 6,048,516 A | 4/2000 | Bringhen et al. |
| 6,123,928 A | 9/2000 | Sovak et al. |
| 6,143,850 A | 11/2000 | Keller et al. |
| 6,183,728 B1 | 2/2001 | Forestier et al. |
| 6,193,959 B1 | 2/2001 | Bernasconi et al. |
| 6,294,156 B1 | 9/2001 | Lentini et al. |
| 6,391,287 B1 | 5/2002 | Baldo et al. |
| 6,413,393 B1 | 7/2002 | Van Antwerp et al. |
| 6,471,949 B2 | 10/2002 | Candau et al. |
| 6,540,986 B2 | 4/2003 | Lukenbach et al. |
| 6,620,407 B1 | 9/2003 | Gers-Barlag et al. |
| 6,620,904 B2 | 9/2003 | Lemke |
| 6,767,547 B2 | 7/2004 | Gers-Barlag et al. |
| 6,800,274 B2 | 10/2004 | Bonda et al. |
| 6,814,959 B1 | 11/2004 | Muller et al. |
| 6,867,250 B1 | 3/2005 | Gupta et al. |
| 6,869,597 B2 | 3/2005 | Arnaud |
| 6,881,415 B1 | 4/2005 | Gers-Barlag et al. |
| 6,899,866 B2 | 5/2005 | Bonda |
| 6,905,674 B2 | 6/2005 | L'Alloret |

(Continued)

FOREIGN PATENT DOCUMENTS

| | | |
|---|---|---|
| EP | 407932 A | 1/1991 |
| EP | 413648 A | 2/1991 |

(Continued)

OTHER PUBLICATIONS

U.S. Appl. No. 61/665,464, filed Jun. 28, 2012, Daly et al.
U.S. Appl. No. 61/665,430, filed Jun. 28, 2012, Levins et al.
U.S. Appl. No. 61/665,439, filed Jun. 28, 2012, Levins et al.
U.S. Appl. No. 61/991,732, filed May 12, 2014, Daly et al.
"Crodacol™ C95 Product Details" from the Croda website, 2013 http://www.croda.com/home.aspx?view=dtl&d=content&s=157&r=401&p=2578&prodID=1779.

(Continued)

*Primary Examiner* — Brian Gulledge

(57) ABSTRACT

Compositions including a discontinuous oil phase homogeneously dispersed in a continuous water phase, the oil phase containing a sunscreen agent that includes a polymer composition containing a linear, ultraviolet radiation absorbing polyether, the linear, ultraviolet radiation absorbing polyether including a chemically bound UV-chromophore; and an oil-in water emulsifier component including an anionic oil-in-water emulsifier in an amount such that the composition includes about 0.5 percent by weight to about 3 percent by weight of the anionic oil-in-water emulsifier.

7 Claims, No Drawings

(56) References Cited

U.S. PATENT DOCUMENTS

| | | | |
|---|---|---|---|
| 6,951,911 B2 | 10/2005 | Tagawa et al. |
| 6,962,692 B2 | 11/2005 | Bonda et al. |
| 6,989,151 B2 | 1/2006 | Gers-Barlag et al. |
| 7,008,618 B1 | 3/2006 | Hessefort et al. |
| 7,087,692 B2 | 8/2006 | Koshti et al. |
| 7,097,828 B2 | 8/2006 | Meyer et al. |
| 7,153,494 B2 | 12/2006 | Chodorowski-Kimmes et al. |
| 7,186,415 B1 | 3/2007 | Gers-Barlag et al. |
| 7,264,795 B2 | 9/2007 | Pflücker et al. |
| 7,427,640 B1 | 9/2008 | Katayama et al. |
| 7,465,438 B2 | 12/2008 | Schunicht et al. |
| 7,534,420 B2 | 5/2009 | Bonda et al. |
| 7,749,524 B2 | 7/2010 | Lu et al. |
| 7,850,954 B2 | 12/2010 | Leblanc et al. |
| 7,914,775 B2 | 3/2011 | Cottard et al. |
| 7,988,953 B2 | 8/2011 | Poschalko et al. |
| 7,993,680 B2 | 8/2011 | Clemente et al. |
| 8,003,132 B2 | 8/2011 | Clemente et al. |
| 8,025,868 B2 | 9/2011 | Clemente et al. |
| 8,211,850 B2 | 7/2012 | Andjelic et al. |
| 8,394,755 B2 | 3/2013 | Andjelic et al. |
| 9,248,092 B2 * | 2/2016 | Daly .................. A61K 8/55 |
| 9,254,254 B2 * | 2/2016 | Daly .................. A61K 8/55 |
| 2001/0038829 A1 | 11/2001 | Hasebe et al. |
| 2002/0131941 A1 | 9/2002 | Habeck et al. |
| 2002/0155073 A1 * | 10/2002 | Fankhauser .......... A61K 8/0241 424/59 |
| 2003/0165553 A1 | 9/2003 | Gers-Barlag et al. |
| 2004/0019220 A1 | 1/2004 | Fischer et al. |
| 2004/0022836 A1 | 2/2004 | Degen et al. |
| 2004/0057914 A1 | 3/2004 | Bonda et al. |
| 2004/0096406 A1 | 5/2004 | De Poilly |
| 2004/0126339 A1 | 7/2004 | Roszell |
| 2004/0197359 A1 | 10/2004 | Yamada et al. |
| 2004/0223925 A1 | 11/2004 | L'Alloret |
| 2004/0228814 A1 | 11/2004 | Candau et al. |
| 2005/0031660 A1 | 2/2005 | Deckner |
| 2005/0036961 A1 | 2/2005 | Hansenne et al. |
| 2005/0048010 A1 * | 3/2005 | Kliss .................. A61K 8/044 424/59 |
| 2005/0065251 A1 | 3/2005 | Candau et al. |
| 2005/0180933 A1 | 8/2005 | Wei et al. |
| 2006/0204457 A1 | 9/2006 | Toda et al. |
| 2007/0098653 A1 | 5/2007 | Tamasawa et al. |
| 2007/0134174 A1 | 6/2007 | Irwin et al. |
| 2008/0081025 A1 * | 4/2008 | Poschalko ........... A61K 8/445 424/60 |
| 2008/0089852 A1 | 4/2008 | Hotz et al. |
| 2008/0247975 A1 | 10/2008 | Dueva-Koganov et al. |
| 2008/0311234 A1 | 12/2008 | Yoneda et al. |
| 2009/0016971 A1 | 1/2009 | Gaudry et al. |
| 2009/0041688 A1 | 2/2009 | Dueva-Koganov et al. |
| 2009/0068130 A1 | 3/2009 | Spaulding et al. |
| 2009/0185988 A1 | 7/2009 | Maleski et al. |
| 2009/0214460 A9 | 8/2009 | Luukas |
| 2009/0232859 A1 | 9/2009 | Sakuta et al. |
| 2009/0258230 A1 | 10/2009 | Schlossman et al. |
| 2009/0297462 A1 | 12/2009 | Hessefort et al. |
| 2009/0324523 A1 | 12/2009 | Clemente et al. |
| 2009/0324524 A1 | 12/2009 | Clemente et al. |
| 2010/0003202 A1 | 1/2010 | Matsumoto et al. |
| 2010/0129303 A1 | 5/2010 | Dueva-Koganov et al. |
| 2010/0189661 A1 | 7/2010 | Musa et al. |
| 2010/0226867 A1 | 9/2010 | Dueva-Koganov et al. |
| 2010/0239508 A1 | 9/2010 | Mori et al. |
| 2010/0284948 A1 | 11/2010 | Ohrmann et al. |
| 2011/0014139 A1 | 1/2011 | Viala et al. |
| 2011/0027202 A1 | 2/2011 | Candau et al. |
| 2011/0104078 A1 | 5/2011 | Burgo et al. |
| 2011/0117034 A1 * | 5/2011 | Satonaka ............. A61K 8/39 424/59 |
| 2011/0195036 A1 | 8/2011 | Clemente et al. |
| 2012/0058974 A1 | 3/2012 | Misske et al. |
| 2012/0087882 A1 | 4/2012 | Fevola et al. |
| 2012/0093753 A1 | 4/2012 | Fevola et al. |
| 2012/0294813 A1 | 11/2012 | Frey et al. |
| 2013/0115179 A1 | 5/2013 | Janssen et al. |
| 2014/0004054 A1 | 1/2014 | Daly et al. |
| 2014/0004055 A1 | 1/2014 | Daly et al. |
| 2014/0004056 A1 | 1/2014 | Daly et al. |
| 2014/0004057 A1 | 1/2014 | Daly et al. |
| 2014/0004058 A1 | 1/2014 | Daly et al. |
| 2014/0004059 A1 | 1/2014 | Daly et al. |
| 2014/0004060 A1 | 1/2014 | Levins et al. |
| 2014/0004061 A1 | 1/2014 | Levins et al. |
| 2014/0004063 A1 | 1/2014 | Daly |
| 2014/0004064 A1 | 1/2014 | Daly |
| 2015/0164771 A1 | 6/2015 | Daly et al. |
| 2015/0320671 A1 | 11/2015 | Daly et al. |

FOREIGN PATENT DOCUMENTS

| | | |
|---|---|---|
| EP | 523955 A | 1/1993 |
| EP | 601080 B | 7/1995 |
| EP | 681830 A | 11/1995 |
| EP | 1051963 A | 11/2000 |
| EP | 1291370 A | 3/2003 |
| EP | 1089986 B | 3/2005 |
| EP | 2015727 B | 1/2010 |
| EP | 2198930 A | 6/2010 |
| EP | 2679616 A | 1/2014 |
| JP | S6099186 A | 6/1985 |
| JP | 2006-265389 A | 10/2006 |
| JP | 2009-167168 A | 7/2009 |
| WO | WO 92/19592 A | 11/1992 |
| WO | WO 93/22366 A | 11/1993 |
| WO | WO 93/22413 A | 11/1993 |
| WO | WO 96/03369 A | 2/1996 |
| WO | WO 01/08647 A | 2/2001 |
| WO | WO 02/24668 A | 3/2002 |
| WO | WO 02/36534 A | 5/2002 |
| WO | WO 2004/009047 A | 1/2004 |
| WO | WO 2005/092282 A | 10/2005 |
| WO | WO 2007/066309 A | 6/2007 |
| WO | WO 2007/081209 A | 7/2007 |
| WO | WO 2008/056678 A | 5/2008 |
| WO | WO 2010/060776 A | 6/2010 |
| WO | WO 2010/115009 A | 10/2010 |
| WO | WO 2011/048570 A | 4/2011 |
| WO | WO 2011/070050 A | 6/2011 |
| WO | WO 2011/070053 A | 6/2011 |
| WO | WO 2011/070073 A | 6/2011 |
| WO | WO 2011/070075 A | 6/2011 |
| WO | WO 2011/070077 A | 6/2011 |
| WO | WO 2014/004474 A | 1/2014 |
| WO | WO 2014/004477 A | 1/2014 |

OTHER PUBLICATIONS

Erberich et al., "Polyglycidols with Two Orthogonal Protective Groups: Preparation, Selective Deprotection, and Functionalization", *Macromolecules* (2007), vol. 40, pp. 3070-3079.

Evans et al., "The Colloidal Domain: where physics, chemistry, biology, and technology meet," Wiley, 1999, p. 409-416; http://www.bre.orst.edu/Courses/Colloid%20Transport/documents/DLVOPrimer.pdf.

Fitton et al., Synthesis (1987), pp. 1140-1142.

Hanson et al., "Sunscreen Enhancement of UV-induced Reactive Oxygen Species in the Skin", *Free Radical Biology & Medicine* (2006) vol. 41, pp. 1205-1212.

Haouet et al., "Preparation Et Proprietes Des Poly®-Glycidols", *European Polymer Journal* (1983), vol. 19(12), pp. 1089-1098. (English Abstract).

Kuhn et al., "Monitoring the Kinetics of Ion-Dependent Protein Folding by Time-Resolved NMR Spectroscopy at Atomic Resolution",*Journal of the American Chemical Society* (2000), vol. 122, pp. 6169-6174.

Lee et al., "Poly(allyl Glycidyl Ether)—A Versatile and Functional Polyether Platform", *Journal of Polymer Science Part A: Polymer Chemistry* (2011), vol. 49, pp. 4498-4504.

Li et al., "Synthesis of polyethylene glycol (PEG) derivatives and PEGylated-peptide biopolymer conjugates", *Biomacromolecules*,

(56) References Cited

OTHER PUBLICATIONS

American Chemical Society, US, vol. 4, No. 4, May 17, 2003, pp. 1055-1067 (ISSN: 1525-7797, DOI: 10.1021/BM034069L) (XP002328259).
Moore et al., "Room Temperature Polyesterification", *Macromolecules* (1990), vol. 23, Issue 1, pp. 65-70.
Obermeier et al., "Poly(ethylene glycol-co-allyl glycidyl ether)s: A PEG-Based Modular Synthetic Platform for Multiple Bioconjugation", Bioconjugate Chemistry (2011), vol. 22, pp. 436-444.
Rokicki et al., "Hyperbranched aliphatic polyethers obtained from environmentally benign monomer: glycerol carbonate", *Green Chemistry* (2005), vol. 7, pp. 529-539.
Stiriba et al., "Hyperbranched molecular nanocapsules: Comparison of the hyperbranched architecture with the perfect linear analogue", Journal of the american Chemical Society (2002) vol. 124, pp. 9698-9699.
Sunder et al., "Controlled Synthesis of Hyperbranched Polyglycerols by Ring-Opening Multibranching Polymerization", *Macromolecules* (1999), vol. 32, pp. 4240-4246.
Taton et al., "Synthesis of chiral and racemic functional polymers from glycidol and thioglycidol", *Macromolecular Chemistry and Physics* (1994), vol. 195, pp. 139-148.
Tchao, "Trans-Epithelial Permeability of Fluorescein in Vitro as an Assay to Determine Eye Irritants", *Alternative Methods in Toxicology 6, Progress in In Vitro Toxicology* (ed.A.M. Goldberg) (1988), pp. 271-283.
Tokar et al., "Cationic Polymerization of Glycidol: Coexistence of the Activated Monomer and Active Chain End Mechanism", *Macromolecules* (1994), vol. 27, pp. 320-322.

\* cited by examiner

SUNSCREEN COMPOSITIONS CONTAINING AN ULTRAVIOLET RADIATION-ABSORBING POLYMER

This application is a continuation of U.S. application Ser. No. 13/926,248, filed on Jun. 25, 2013, which claims the benefit of U.S. provisional application 61/665,464 filed Jun. 28, 2012, the complete disclosure of which is hereby incorporated herein by reference for all purposes.

FIELD OF THE INVENTION

The present invention relates to topically-acceptable sunscreen compositions comprising UV-absorbing polyethers.

BACKGROUND OF THE INVENTION

The prolonged exposure to ultraviolet (UV) radiation, such as from the sun, can lead to the formation of light dermatoses and erythemas, as well as increase the risk of skin cancers, such as melanoma, and accelerate skin aging, such as loss of skin elasticity and wrinkling.

Numerous sunscreen compositions are commercially available with varying ability to shield the body from ultraviolet light. However, numerous challenges still exist to provide sunscreen compositions that provide strong UV radiation protection.

The challenge of creating sunscreens with various properties, e.g., mildness, etc., is further magnified if one imposes additional constraints on the sunscreen composition. The present invention provides mild, aesthetic sunscreen compositions that include a polymeric sunscreen compound.

SUMMARY OF THE INVENTION

According to one aspect, compositions of the present invention include a discontinuous oil phase that includes a sunscreen agent comprising a polymer composition that includes a linear, ultraviolet radiation absorbing polyether that comprises a chemically bound UV-chromophore. The discontinuous oil phase is homogeneously distributed in a continuous water phase. The composition further comprises an oil-in-water emulsifier component comprising an anionic oil-in-water emulsifier in an amount of about 0.5 percent to about 3 percent by weight of said composition.

DETAILED DESCRIPTION OF THE INVENTION

Unless defined otherwise, all technical and scientific terms used herein have the same meaning as commonly understood by one of ordinary skill in the art to which the invention belongs. As used herein, unless otherwise indicated, all hydrocarbon groups (e.g., alkyl, alkenyl) groups may be straight or branched chain groups. As used herein, unless otherwise indicated, the term "molecular weight" refers to weight average molecular weight, (Mw).

Unless defined otherwise, all concentrations refer to concentrations by weight of the composition. Also, unless specifically defined otherwise, the term "essentially free of," with respect to a class of ingredients, refers to the particular ingredient(s) being present in a concentration less than is necessary for the particularly ingredient to be effective to provide the benefit or property for which it otherwise would be used, for example, about 1% or less, or about 0.5% or less.

As used herein, "UV-absorbing" refers to a material or compound, e.g. a polymeric or non-polymeric sunscreen agent or a chemical moiety, which absorbs radiation in some portion of the ultraviolet spectrum (290 nm-400 nm), such as one having an extinction coefficient of at least about 1000 $mol^{-1}$ $cm^{-1}$, for at least one wavelength within the above-defined ultraviolet spectrum. SPF values disclosed and claimed herein are determined using the in-vitro method described herein below.

UV-Absorbing Polyether

Embodiments of the invention relate to compositions including an ultraviolet radiation absorbing polyether, (i.e., "UV absorbing polyether"). By UV absorbing polyether, it is meant a polyether that absorbs radiation in some portion of the ultraviolet spectrum (wavelengths between 290 and 400 nm). The UV absorbing polyether has a weight average molecular weight ($M_w$), which may be suitable for reducing or preventing the chromophore from absorbing through the skin. According to one embodiment, a suitable molecular weight for the UV absorbing polyether is $M_w$ greater than 500. In one embodiment, $M_w$ is in the range of about 500 to about 50,000. In another embodiment, the $M_w$ is in the range of about 1,000 to about 20,000, such as from about 1,000 to about 10,000.

Described herein is a composition including a UV-absorbing polyether. As one skilled in the art will recognize, "polyether" indicates that the UV absorbing polymer includes a plurality of ether functional groups covalently bonded to each other. The "backbone" of the UV-absorbing polyether refers to the longest continuous sequence of covalently bonded ether functional groups. Other smaller groups of covalently bonded atoms are considered pendant groups that branch from the backbone.

According to certain embodiments the UV-absorbing polyether includes glyceryl repeat units and accordingly, may be characterized as a polyglycerol. By "glyceryl repeat units" (also referred to herein "glyceryl remnant units") it is meant glycerol units excluding nucleophilic groups such as hydroxyl groups. Glyceryl remnant units include ether functional groups, and generally may be represented as $C_3H_5O$ for linear and dendritic remnants (Rokicki et al. *Green Chemistry.*, 2005, 7, 52). Suitable glyceryl remnant units include dehydrated forms (i.e. one mole of water removed) of the following glyceryl units: linear-1,4 ($L_{1,4}$) glyceryl units; linear-1,3 ($L_{1,3}$) glyceryl repeat units; dendritic (D) glyceryl units; terminal-1,2 ($T_{1,2}$) units; and terminal-1,3 ($T_{1,3}$) units. Examples of linear glyceryl remnant units and terminal units are shown below (to the right side of the arrows). The corresponding glyceryl unit before dehydration (shown to the left side of arrows; includes hydroxyls) are shown as well:

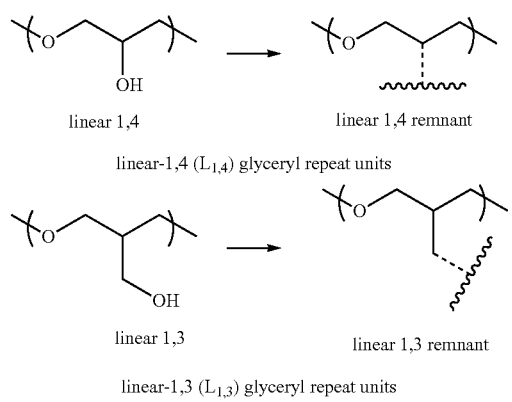

linear 1,4      linear 1,4 remnant linear-1,4 ($L_{1,4}$) glyceryl repeat units linear 1,3      linear 1,3 remnant linear-1,3 ($L_{1,3}$) glyceryl repeat units

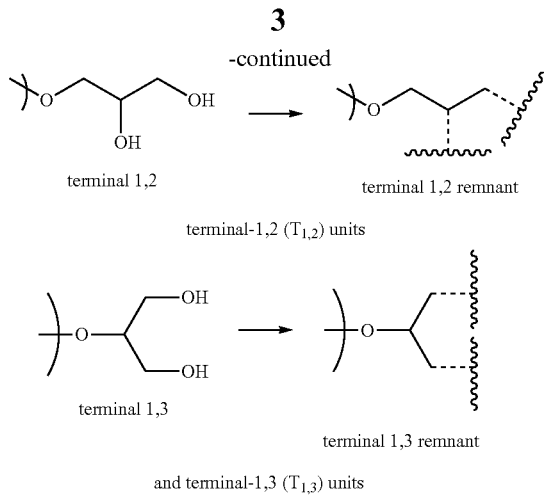

terminal 1,2 → terminal 1,2 remnant terminal-1,2 ($T_{1,2}$) units

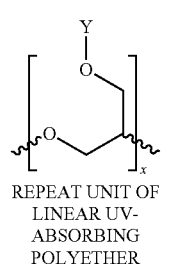

terminal 1,3 → terminal 1,3 remnant and terminal-1,3 ($T_{1,3}$) units

The composition includes a linear UV-absorbing polyether that comprises a chemically bound ultraviolet radiation-absorbing chromophore ("UV-chromophore"). By linear, it is meant the UV-absorbing polyether has a backbone that is unbranched.

According to certain embodiments, the linear UV-absorbing polyether includes either or both of the repeat units shown in FORMULA IA and FORMULA IIB, below:

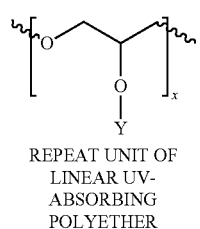

REPEAT UNIT OF LINEAR UV-ABSORBING POLYETHER

FORMULA IA

FORMULA IIB

REPEAT UNIT OF LINEAR UV-ABSORBING POLYETHER

In FORMULAS IA and IIB, Y represents a UV-chromophore, as described below. An illustrative example of a linear UV-absorbing polyether that comprises a chemically bound UV-chromophore is shown in FORMULA IIIC.

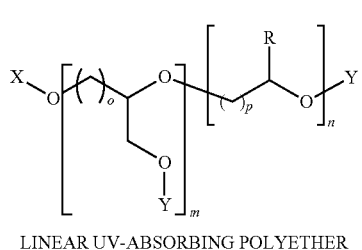

LINEAR UV-ABSORBING POLYETHER

FORMULA IIIC

In the structure illustrated in FORMULA IIIC, X is either a terminal functional group or part of the polymer backbone; R is a pendant group attached to the polymer backbone, and X is a terminal group.

X and R may either be the same or different. X and R may be independently selected from, for example, hydrogen, linear alkyl, alkenyl or alkynyl hydrocarbon chains, linear siloxanes, and the like. In one embodiment the group X represents octadecane. Y represents a UV-chromophore and the groups represented by Y are described below. The proportion of ether repeat units bearing substituent Y is a real number expressed by Equation 1, $$\frac{m}{n+m} \qquad \text{Equation 1}$$

where m and n both represent a real number between 0 and 1, and the sum of n and m equals 1. In one embodiment, the number m=1 and n=0 (the UV-absorbing polyether is a homopolymer and includes the repeat unit of FORMULA IA). In another embodiment, the number m<1 (the polymer is a copolymer) with R and Y pendant groups. For copolymers containing both R and Y pendant groups, the distribution of the pendant R and Y groups along the polymer chain can be modified to obtain optimal polymer properties. In one embodiment, the UV-absorbing polyether is a random copolymer, and the groups R and Y are statistically distributed along the polymer chain. In another embodiment, the UV-absorbing polyether is a block copolymer, consisting of alternating segments of polymer backbone functionalized with a greater proportion of either R or Y. In another embodiment, the distribution of the pendant groups R and Y along the polymer backbone is somewhere between the boundary conditions of block and statistically random copolymers. In FORMULA IIIC, the integers o and p represent the number of $CH_2$ groups in the repeat units bearing Y and R.

Introduction of varied R pendant groups can be achieved through the use of other co-monomers during the polymerization reaction. The size, chemical composition, weight percent and position in the backbone of these co-monomers can be varied to change the physical and chemical properties of the final UV-absorbing polyether. Examples of co-monomers that can be incorporated into the UV-absorbing polyether include, but are not limited to, ethylene oxide, propylene oxide, and glycidyl ethers such as n-butyl glycidyl ether, 2-ethylhexylglycidyl ether.

It is clear to one skilled in the art that polyethers of the type illustrated in FORMULAS IA, IIB and IIIC can be obtained through various synthetic routes. Among these routes is ring-opening polymerization of cyclic ether monomers and optional co-monomers. The size of the ring in the cyclic ether monomers determines the values of o or p, and the resulting backbone structure of the UV-absorbing polyether. For monomers or co-monomers that are epoxides (three-membered rings containing two carbon atoms and one oxygen atom), the value of o or p in the resulting UV-absorbing polyether is 1. A repeat unit that results from using an epoxide co-monomer is shown in structure A of FORMULA IV. For (co)monomers that are oxetanes (four-membered rings containing three carbon atoms and one oxygen atom), the value of o or p in the resulting UV absorbing polyether is 2. A repeat unit that results from using an oxetane co-monomer is shown in structure B of FORMULA IV. The length of the alkyl chain within each monomer type can be selected to modify the properties of the UV-absorbing polyether. In one embodiment, both o and p equal 1. An example of this case is if the repeat units bearing Y and R both are derived from epoxide monomers (o=p=1), or both derived from oxetane monomers (o=p=2). In another embodiment, o and p are not equal. An example of this case is if the repeat units bearing the UV-chromophore Y are based on an epoxide monomer (o=1), and the repeat units bearing the group R are based on an oxetane monomer (p=2).

FORMULA IV

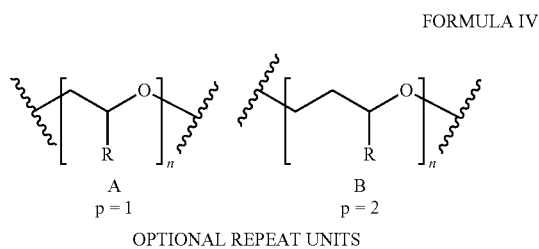

A
p = 1

B
p = 2

OPTIONAL REPEAT UNITS

Suitable UV-chromophores that may be chemically bound in UV-absorbing polyethers of the present invention include UV-absorbing triazoles (a moiety containing a five-membered heterocyclic ring with two carbon and three nitrogen atoms), such as benzotriazoles. In another embodiment, the structure represented by Y contains or has a pendant UV-absorbing triazine (a six membered heterocycle containing three nitrogen and three carbon atoms). Suitable UV-chromophores include those that have absorbance of UVA radiation. Other suitable UV-chromophores are those which have absorbance in the UVB region. In one embodiment, the UV-chromophore absorbs in both the UVA and UVB region. In one embodiment, when the UV-absorbing polyether is cast into a film, it is possible to generate a molar extinction coefficient measured for at least one wavelength in this wavelength range of at least about 1000 $mol^{-1}$ $cm^{-1}$, preferably at least about 2000 $mol^{-1}$ $cm^{-1}$, more preferably at least about 4000 $mol^{-1}$ $cm^{-1}$. In one embodiment, the molar extinction coefficient among at least 40% of the wavelengths in this portion of the spectrum is at least about 1000 $mol^{-1}$ $cm^{-1}$. Examples of UV-chromophores that are UVA absorbing include triazoles such as benzotriazoles, such as hydroxyphenyl-benzotriazoles; camphors such as benzylidene camphor and its derivatives (such as terephthalylidene dicamphor sulfonic acid); dibenzoylmethanes and their derivatives.

In one embodiment, the UV-chromophore is a benzotriazole providing both photostability and strong UVA absorbance with a structure represented in FORMULA V.

FORMULA V

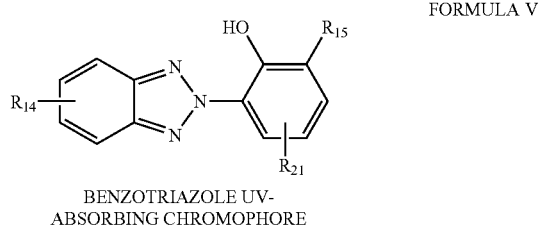

BENZOTRIAZOLE UV-
ABSORBING CHROMOPHORE wherein each $R_{14}$ is independently selected from the group consisting of hydrogen, $C_1$-$C_{20}$ alkyl, alkoxy, acyl, alkyloxy, alkylamino, and halogen; $R_{15}$ is independently selected from the group consisting of hydrogen, $C_1$-$C_{20}$ alkyl, alkoxy, acyl, alkyloxy, and alkylamino, $R_{21}$ is selected from $C_1$-$C_{20}$ alkyl, alkoxy, acyl, alkyloxy, and alkylamino. Either of the $R_{15}$ or $R_{21}$ groups may include functional groups that allow attachment to a polymer. Compounds resembling the structure in FORMULA V are described in U.S. Pat. No. 5,869,030, and include, but are not limited to, methylene bis-benzotriazolyl tetramethylbutylphenol (a compound sold under the trade name TINSORB M by BASF Corporation, Wyandotte, Mich.). In one embodiment, the UV-absorbing triazole is derived from a transesterification product of 3-(3-(2H-benzo[d][1,2,3]triazol-2-yl)-5-(tert-butyl)-4-hydroxyphenyl)propanoic acid with polyethylene glycol 300, commercially available as TINUVIN 213, also available from BASF. In another embodiment, the UV-absorbing triazole is Benzenepropanoic acid, 3-(2H-benzotriazol-2-yl)-5-(1,1-dimethylethyl)-4-hydroxy-, $C_{7-9}$-branched and linear alkyl esters, commercially available as TINUVIN 99, also available from BASF. In another embodiment, the UV-absorbing group contains a triazine moiety. An exemplary triazine is 6-octyl-2-(4-(4,6-di([1,1'-biphenyl]-4-yl)-1,3,5-triazin-2-yl)-3-hydroxyphenoxy)propanoate (a compound sold under the trade name TINUVIN 479 by BASF Corporation, Wyandotte, Mich.).

In another embodiment, the UV-chromophore is a UVB-absorbing moiety. By UVB-absorbing chromophore it is meant that the UV-chromophore has absorbance in the UVB portion (290 to 320 nm) of the ultraviolet spectrum. In one embodiment, the criteria for consideration as a UVB-absorbing chromophore is similar to those described above for an UVA-absorbing chromophore, except that the wavelength range is 290 nm to 320 nm. Examples of suitable UVB-absorbing chromophores include 4-aminobenzoic acid and alkane esters thereof; anthranilic acid and alkane esters thereof; salicylic acid and alkane esters thereof; hydroxycinnamic acid alkane esters thereof; dihydroxy-, dicarboxy-, and hydroxycarboxybenzophenones and alkane ester or acid halide derivatives thereof; dihydroxy-, dicarboxy-, and hydroxycarboxychalcones and alkane ester or acid halide derivatives thereof; dihydroxy-, dicarboxy-, and hydroxycarboxycoumarins and alkane ester or acid halide derivatives thereof; benzalmalonate (benzylidene malonate); benzimidazole derivatives (such as phenyl benzilimazole sulfonic acid, PBSA), benzoxazole derivatives, and other suitably functionalized species capable of copolymerization within the polymer chain. In another embodiment, the UV-absorbing polyether includes more than one UV-chromophore or more than one chemical class of UV-chromophore.

UV-absorbing polyethers useful in the present invention may be synthesized by, according to certain embodiments, ring-opening polymerization of a suitable cyclic ether monomer to form a polyether, followed by covalent attachment of UV-chromophores to pendant functional groups ("post-polymerization attachment"). According to certain other embodiments, the UV-absorbing polyethers may be synthesized by polymerization of a cyclic ether monomer, wherein the monomer itself includes a covalently attached UV-chromophore (i.e., "direct polymerization").

Furthermore, as one skilled in the art will recognize, the UV-absorbing polyethers that are useful in topical compositions of the present invention are prepared via polymer synthesis. Synthesis of the UV-absorbing polyether generally results in a reaction product, hereinafter referred to as a "polymer composition", that is a mixture of various molecular weights of UV-absorbing polyethers. The polymer composition may further include (apart from the UV-absorbing polyether) a small amount of unpolymerized material which may be removed using techniques known in the art. According to certain embodiments, the unpolymerized material (e.g., partially reacted or unreacted monomers or other reactants) may be partially or completely removed before inclusion in the topical compositions of the present invention, using for example, solvent extraction or supercritical $CO_2$ purification.

According to certain embodiments, the polymer composition to be incorporated into topical compositions of the present invention comprises about 50% or more of the linear UV-absorbing polyether that comprises a chemically bound UV-chromophore. According to certain other embodiments, the polymer composition comprises about 75% or more of the linear UV-absorbing polyether that comprises a chemically bound UV-chromophore. According to certain other embodiments, the polymer composition comprises about 90% or more of the linear UV-absorbing polyether, such as about 95% or more. According to certain other embodiments, in addition to the linear UV-absorbing polyether, the polymer composition comprises a branched UV-absorbing polyether that is not hyperbranched. In another embodiment, the polymer composition is substantially free of hyperbranched UV-absorbing polyethers (e.g., includes less than about 1% by weight of hyperbranched UV-absorbing polyether, such as less than about 0.1% by weight, such as completely free of hyperbranched UV-absorbing polyethers.

According to certain embodiments, the polymer composition has a low polydispersity. For example, the polydispersity index of the polymer composition may be about 1.5 or less, such as about 1.2 or less. Polydispersity index is defined as $M_w/M_N$ (i.e., the ratio of weight average molecular weight, $M_w$ to number average molecular weight, $M_N$). According to certain other embodiments, the polymer composition includes 50% or more by weight of a particular UV-absorbing polyether molecule.

Polydispersity of the polymer composition may be kept low using, for example, particular synthetic procedures, such as ring-opening polymerization of a cyclic ether monomer and deprotection (described below). Alternatively, or in addition, the polymer composition may be treated using techniques known in the art, such as supercritical $CO_2$ to purify the polymer composition (e.g., before or after attachment of UV-chromophore).

Synthesis of the linear, UV-absorbing polyether by post-polymerization attachment of the UV-chromophore may include the steps of ring-opening polymerization of a cyclic ether monomer to form a polyether having protected groups; deprotecting the polyether to remove at least some of the protected groups; and attaching a UV-chromophore to the deprotected UV-absorbing polyether to form a UV-absorbing polyether having a chemically bound UV chromophore.

An example of forming the linear, UV-absorbing polyether post-polymerization attachment is illustrated schematically in FORMULA VI. An initiator I is used to induce polymerization of cyclic ether monomer M, generating polymer $P_0$ wherein pendant hydroxy functional groups are protected with a protecting group (P). Polymer $P_0$ is subjected to conditions that remove protecting group P, affording deprotected polymer $P_d$. Finally, UV-chromophore Y is attached to the pendant hydroxyl groups of polymer $P_d$, affording the desired final polymer, $P_f$.

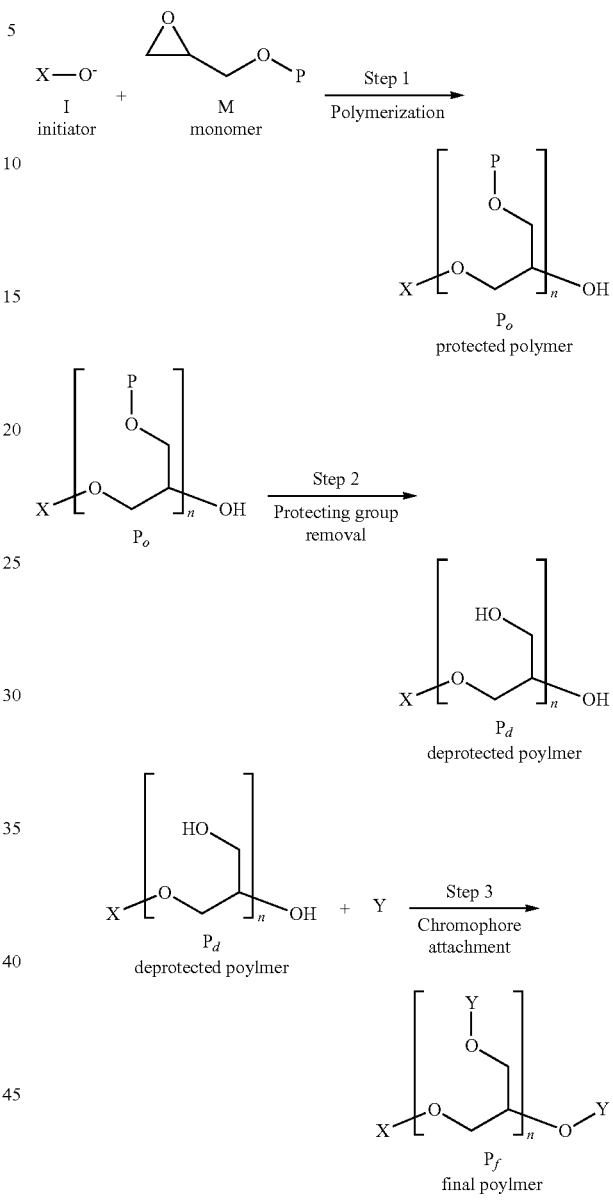

Ring-opening polymerization of cyclic ethers such as monomer M in FORMULA VI can be achieved using various methods including cationic and anionic ring-opening polymerization. In one embodiment, the polymerization is performed by anionic ring opening polymerization. Monomer M in FORMULA VI is a form of glycidol wherein the primary hydroxy group has been masked with protecting group P. Polymerization of unprotected glycidol results in the formation of highly branched polymers (U.S. Pat. No. 7,988,953B2, Tokar, R. et. al. *Macromolecules* 1994, 27, 320-322: Sunder, A. et. al. *Macromolecules* 1999: 4240-4246. Rokicki, G. et. al. *Green Chemistry* 2005, 7, 529). Conversely, anionic polymerization of glycidol derivatives where the primary hydroxyl group has been protected can generate linear polyethers, as illustrated by structure $P_0$ in FORMULA VI (Taton, D. et. al. *Macromolecular Chemistry* and *Physics* 1994, 195, 139-148: Erberich, M. et. al. *Macromolecules* 2007, 40, 3070-3079: Haouet, A. et. al. *European Polymer Journal* 1983, 19, 1089-1098: Obermeier, B. et. al *Bioconjugate Chemistry* 2011, 22, 436-444: Lee, B. F. et. al. *Journal of polymer science. Part A, Polymer chemistry* 2011, 49, 4498-4504). The protected cyclic ether monomer is not limited to epoxide derivates, and includes functionalized cyclic ethers containing 3 through 6 contiguous atoms; in another embodiment, the monomer M is an oxetane derivative containing a protected primary hydroxyl group.

By protected, it is meant that a functional group in a multifunctional molecule has been selectively derivatized with a moiety that prevents covalent modification at that functional group. Moieties that are used as protecting groups are typically attached to the desired functional groups with excellent chemical yield, and can be selectively removed as required in good yield, revealing the original functional group. Hydroxyl protecting groups include but are not limited to ethers such as methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), allyl, 3-bromotetrahydropyranyl, tetrahydrothiopyranyl, 1-methoxycyclohexyl, benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, trimethylsilyl (TMS), triethylsilyl (TES), trii sopropylsilyl (TIPS), t-butyldimethylsilyl (TBDMS), t-butyldiphenylsilyl (TBDPS), tribenzylsilyl, esters such as formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate(levulinate), 4,4-(ethylenedithio)pentanoate(levulinoyldithioacetal), pivaloate, adamantoate, crotonate, 4-methoxycrotonate, benzoate, p-phenylbenzoate, 2,4,6-trimethylbenzoate(mesitoate), and carbonates such as alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate. In one embodiment, the protecting group is ethoxyethyl ether; in another embodiment, the protecting group is allyl ether.

Removal of protecting groups from the protected linear polyether $P_0$ to generate deprotected polymer $P_d$ is achieved using methods complimentary to the choice of protecting group P; such methods are familiar to those skilled in the art. In one embodiment, the primary hydroxyl group of the cyclic ether monomer is protected as the 1-ethoxyethyl ether; the cleavage of this protecting group to generate the deprotected polymer is achieved using aqueous acidic conditions such as aqueous acetic acid, aqueous hydrochloric acid, or acidic ion exchange resin. In another embodiment, the primary hydroxyl group of the cyclic ether monomer protected as an allyl ether; the cleavage of this protecting group to generate the deprotected polymer is achieved by isomerizaion of the allyl ether to the vinyl ether by treatment with potassium alkoxide followed by treatment with aqueous acid, isomerization using transition metal catalysts followed by acidic hydrolysis, or direct removal using palladium (0) catalysts and a nucleophilic scavenger.

The anionic ring-opening polymerization of monomer M illustrated in FORMULA VI is initiated by alkoxide salt I. Examples of alkoxides suitable for initiation of ring-opening polymerization of cyclic ether monomers include, but are not limited to the potassium salts of linear $C_3$ through $C_{30}$ hydrocarbon alcohols, polyethylene glycol methyl ether, and carbinol terminated polysiloxanes. In one embodiment, the initiator for anionic ring-opening polymerization is the potassium salt of octadecanol. Another embodiment of the current invention makes use of a multifunctional initiator including, but not limited to polyoxyalkylenes such as polyethylene glycol, polypropylene glycol or poly(tetramethylene ether)glycol; polyesters such as poly(ethyleneadipate), poly(ethylenesuccinate); copolymers that have both oxyalkylene and ester functionality in the backbone such as poly[di(ethylene glycol)adipate]; and lower molecular weight alcohols such as 1,4-butanediol, 1,6-hexanediol or neopentyl glycol.

Depending on the functional groups pendant from the polyether, chromophores can be covalently attached to the polymer backbone using a variety of methods known to those skilled in the art. The following methods are illustrative, and do not represent an exhaustive list of the possible means to attach a UV-chromophore to the polymer backbone. In the case of polymers with free hydroxyl groups (as represented by structure $P_d$ in FORMULA VI) a UV-chromophore containing a carboxylate group may be covalently attached to the polymer using a number of methods familiar to those skilled in the art. Condensation reagents can be used to form covalent bonds between UV-chromophores with carboxylic acids and hydroxyl groups on polymers generating ester bonds; in one embodiment, the condensation reagent is N-(3-dimethylaminopropyl)-N'-ethylcarbodiimide hydrochloride. The carboxylic acid of the UV-chromophore may also be attached to hydroxyl groups on the polymer through ester bonds using transition metal catalysis; in one embodiment, the catalyst is tin (II) ethylhexanoate. The UV-chromophore can also be attached to the polymer by converting the carboxylic acid of the UV-chromophore to the corresponding acid chloride; the acid chloride reacts with hydroxyl groups on the functional polymer forming ester bonds; in one embodiment, this conversion to the acid chloride is performed using thionyl chloride. The UV-chromophore carboxylic acid may also be converted to the isocyanate through Curtius rearrangement of an intermediate acid azide; the chromophore isocyanate reacts with hydroxyl groups on the functional polymer forming a urethane bonds. In another embodiment, the carboxylic acid on the UV-chromophore can be converted to an ester, and attached to the hydroxyl group on the backbone by transesterification. This can be achieved by conversion of the carboxylic acid to an ester with a low boiling alcohol such as methanol; transesterification is performed by reacting the chromophore ester with the polymer containing side chain hydroxyl groups using an acid catalyst, for instance, paratoluene sulfonic acid.

Also in the case of polyethers with free hydroxyl groups, a UV-chromophore containing a hydroxyl group may be covalently attached to the polyether using a number of methods familiar to those skilled in the art. In one embodiment, the hydroxyl group on the UV-chromophore can be activated for nucleophilic displacement using a reagent such as methane sulfonyl chloride or p-toluene sulfonyl chloride; the hydroxyl groups on the backbone are then able to displace the resulting mesylate or tosylate under basic conditions to generate an ether bond between the polymer and the UV-chromophore. In another embodiment, the hydroxyl group on the UV-chromophore can be converted to the chloroformate using a reagent such as phosgene, diphosgene, or triphosgene; the resulting UV-chromophore chloroformate can react with hydroxyl groups on the backbone of the polymer to generate a carbonate bond between the polymer and the UV-chromophore. In the case of polymers with free hydroxyl groups (as represented by structure $P_d$ in FORMULA VI) a UV-chromophore containing an amine group may be covalently attached to the polymer using a number of methods familiar to those skilled in the art. In one embodiment, the hydroxyl groups on the polymer can be converted to the corresponding chloroformates using a reagent such as phosgene, diphosgene and triphosgene; the amine functionalized UV-chromophore can then react with the polymer chloroformates generating a carbamate bond between the UV-chromophore and polyether.

In another embodiment, some of the hydroxyl groups on the linear polyether backbone remain after the acid, acid chloride or isocyanate functional UV-chromophores are attached. These unreacted hydroxyl groups may be used to attach other monofunctional side groups to improve the physical and chemical properties of the polymer. Examples of hydroxyl reactive functional groups include, but are not limited to, acid chlorides and isocyanates. Specific examples of hydroxyl reactive functional side groups include palmitoyl chloride and stearyl isocyanate. Other examples of groups that may be pendant from polymers that are sites for covalent attachment of UV-chromophores include, but are not limited to, conjugated alkenes, amines, and carboxylic acids.

In a another embodiment, the polyether backbone is a polyglycerol with pendant hydroxyl groups or hydrophobic groups, such as a polyglyceryl ester, for example, decaglyceryl monostearate sold under the tradename POLYALDO 10-1-S by Lonza in Allendale, N.J. or tetradecaglyceryl monostearate sold under the tradename POLYALDO 14-1-S by Lonza in Allendale, N.J. The pendant hydroxyl groups may be reacted with a UV-chromophore containing a complementary functional group as described above to obtain a UV absorbing polyether. In this embodiment, the polymer composition will be, for example, the reaction product of a polyglycerol ester and a UV chromophore having a functional group suitable for covalent attachment to said polyglycerol ester. Suitable functional groups on the UV chromophore include carboxylates, isocyanates, among other functional groups discussed previously. The resulting polymer composition may include a linear UV-absorbing polyether having the repeat unit shown in FORMULA IIB. The resulting polymer composition may further include some non-linear (e.g., cyclic components) as well, depending upon the percentage of linear material present in the polyglycerol.

As described above, the synthesis of suitable polymer compositions containing the UV-absorbing polyethers could also be achieved through polymerization of UV-chromophores covalently modified with cyclic ether groups (direct polymerization). This is illustrated in FORMULA VII, where Y represents a UV-chromophore, and o is a characteristic of the ring size of the cyclic ether monomer.

FORMULA VII. DIRECT POLYMERIZATION OF UV-CHROMOPHORE COVALENTLY ATTACHED TO CYCLIC ETHER

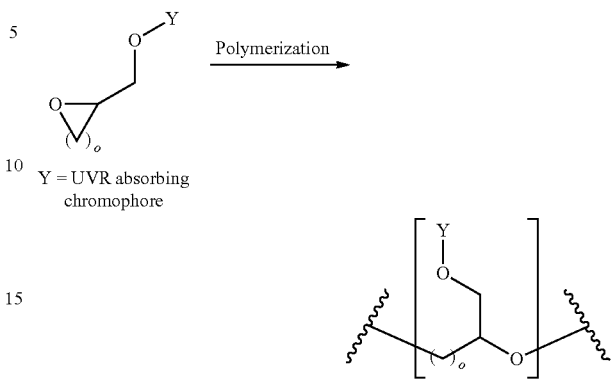

Y = UVR absorbing chromophore

The polymer compositions described herein are useful in applications where UV absorption is desired. For example, the polymer composition may be useful for combining with a suitable cosmetically acceptable carrier for cosmetic applications or combining the polymer composition with other materials to reduce UV degradation of the materials (i.e., melt blending the material with the polymer composition or coating the material with the polymer composition). The incorporation of UV-absorbing polyethers into such compositions of the present invention may provide enhanced SPF (primarily UVB absorbance), enhanced PFA (primarily UVA absorbance) or enhancement of both. The cosmetically-acceptable topical carrier is suitable for topical application to human skin and may include for example, one or more of vehicles such as water, ethanol, isopropanol, emollients, humectants, and/or one or more of surfactants/emulsifiers, fragrances, preservatives, water-proofing polymers, and similar ingredients commonly used in cosmetic formulations. As such, the polymer composition may be formulated using ingredients known in the art into a spray, lotion, gel, stick or other product forms. Similarly, according to certain embodiments, one may protect human skin from UV radiation by topically applying a composition comprising the polymer composition containing the UV-absorbing polyether.

According to certain embodiments, the sunscreen agent present in topical compositions of the present invention may consist of, or consists essentially of, the UV-absorbing polyether, as defined herein. According to certain other embodiments, the sunscreen agent may include additional UV-absorbing polymers, other than the UV-absorbing polyethers, as defined herein, and/or non-UV-absorbing, light-scattering particles. Additional UV-absorbing polymers are molecules that can be represented as having one or more structural units that repeat periodically, e.g., at least twice, to generate the molecule, and may be UV-absorbing polyethers, other than those used in compositions as defined and claimed in this specification. In certain embodiments, the compositions may be substantially free of UV-absorbing polymers other than the UV-absorbing polyethers. In yet other embodiments, the compositions may be substantially free of both UV-absorbing polymers other than the UV-absorbing polyethers and non-polymeric UV-absorbing sunscreen agents (described below).

Additional UV-absorbing polymers may have a molecular weight of greater than about 1500. Examples of suitable additional UV-absorbing polymers include benzylidene malonate silicone, including those described in U.S. Pat. No. 6,193,959, to Bernasconi et al. A particularly suitable benzylidene malonate includes "Parsol SLX," commercially available from DSM (Royal DSM N.V.) of Heerlen, Netherlands. Other suitable additional UV-absorbing polymers are disclosed in U.S. Pat. No. 6,962,692; U.S. Pat. No. 6,899,866; and/or U.S. Pat. No. 6,800,274; including hexanedioic acid, polymer with 2,2-dimethyl-1,3-propanediol, 3-[(2-cyano-1-oxo-3,3-diphenyl-2-propenyl)oxy]-2,2-dimethylpropyl 2-octyldodecyl ester; sold under the trade name "POLYCRYLENE," commercially available from the HallStar Company of Chicago, Ill. When utilized, such additional UV-absorbing polymers may be used at concentrations of about 1% or more, for example about 3% or more.

Non-UV-absorbing, light-scattering particles do not absorb in the UV spectrum, but may enhance SPF by scattering of the incident UV radiation. Examples of non-UV-absorbing, light-scattering particles include solid particles having a dimension, e.g., average diameter, from about 0.1 micron to about 10 microns. In certain embodiments, the non-UV-absorbing, light-scattering particle is a hollow particle comprising, or consisting essentially of, an organic polymer or a glass. Suitable organic polymers include acrylic polymers, including acrylic/styrene copolymers, such as those known as SUNSPHERES, which are commercially available from Dow Chemical of Midland, Mich. Suitable glasses include borosilicate glasses such as those described in published United States Patent Application US20050036961A1, entitled, "AESTHETICALLY AND SPF IMPROVED UV-SUNSCREENS COMPRISING GLASS MICROSPHERES".

Topical Composition

In one embodiment, a composition suitable for topical/cosmetic use for application to the human body, e.g., keratinaceous surfaces such as the skin, hair, lips, or nails, and especially the skin, is provided. The composition includes the polymer composition comprising the one or more linear UV-absorbing polyethers that comprise a chemically bound UV-chromophore.

As discussed above, the concentration of the UV-absorbing polyether in the topical composition may be sufficient to provide an SPF of about 10 or greater, particularly in the absence or substantial absence of the additional UV-absorbing polymers or non-polymeric UV-absorbing sunscreen agents as described herein. Accordingly, the concentration of the ultraviolet radiation absorbing polyether may vary from about 5% to about 50%, such as from about 7% to about 40%, such as from about 10% to about 25% of the topical composition. In certain embodiments, the concentration of UV-absorbing polyether is about 10% or more, such as about 15% or more, such about 25% or more of the composition. According to certain embodiments where the sunscreen agent consists essentially of the UV-absorbing polyether, the concentration of the UV-absorbing polyether may be about 15% or more.

The concentration of non-UV-absorbing light-scattering particles, if present, may be about 1% or more, such as from about 1% to about 10%, such as from about 2% to about 5%. In certain embodiments where the UV-sunscreen agent further includes a non-UV-absorbing sunscreen agent in amounts as discussed above, compositions of the present invention may have an SPF of about 20 or greater.

Compositions of the present invention may, according to certain embodiments, be substantially free of non-polymeric UV-absorbing sunscreen agents. By "substantially free of non-polymeric UV-absorbing sunscreen agents," it is meant that, in this embodiment, the compositions do not contain non-polymeric UV-absorbing sunscreen agents in an amount effective to provide the compositions with an SPF of greater than 2 in the absence of the UV-absorbing polyether, as determined via the in vitro method described herein below. For example, the compositions of the invention will contain about 1% or less, or about 0.5% or less, of such non-polymeric UV-absorbing sunscreen agents. One example of non-polymeric UV-absorbing sunscreen agents that the composition is substantially free of typically may be characterized as "organic" (include predominantly or only atoms selected from carbon, hydrogen, oxygen, and nitrogen) and having no definable repeat unit and typically having molecular weights that are about 600 daltons or less, such as about 500 daltons or less, such as less than 400 daltons. Examples of such compounds, sometimes referred to as "monomeric, organic UV-absorbers" include, but are not limited to: methoxycinnamate derivatives such as octyl methoxycinnamate and isoamyl methoxycinnamate; camphor derivatives such as 4-methyl benzylidene camphor, camphor benzalkonium methosulfate, and terephthalylidene dicamphor sulfonic acid; salicylate derivatives such as octyl salicylate, trolamine salicylate, and homosalate; sulfonic acid derivatives such as phenylbenzimidazole sulfonic acid; benzone derivatives such as dioxybenzone, sulisobenzone, and oxybenzone; benzoic acid derivatives such as aminobenzoic acid and octyldimethyl para-amino benzoic acid; octocrylene and other β,β-diphenylacrylates; dioctyl butamido triazone; octyl triazone; butyl methoxydibenzoyl methane; drometrizole trisiloxane; and menthyl anthranilate.

Other non-polymeric UV-absorbing sunscreen agents that the composition may be substantially free of may include ultraviolet-absorbing particles, such as certain inorganic oxides, including titanium dioxide, zinc oxide, and certain other transition metal oxides. Such ultraviolet screening particles are typically solid particles having a diameter from about 0.1 micron to about 10 microns.

The compositions of the present invention may be used for a variety of cosmetic uses, especially for protection of the skin from UV radiation. The compositions, thus, may be made into a wide variety of delivery forms. These forms include, but are not limited to, suspensions, dispersions, solutions, or coatings on water soluble or water-insoluble substrates (e.g., substrates such as organic or inorganic powders, fibers, or films). Suitable product forms include lotions, creams, gels, sticks, sprays, ointments, mousses, and compacts/powders. The composition may be employed for various end-uses, such as recreation or daily-use sunscreens, moisturizers, cosmetics/make-up, cleansers/toners, anti-aging products, or combinations thereof. The compositions of the present invention may be prepared using methodology that is well known by an artisan of ordinary skill in the field of cosmetics formulation.

Compositions of the present invention include a continuous water phase in which a discontinuous oil phase that includes the UV-absorbing polyether is homogeneously distributed. In certain embodiments, the UV-absorbing polyether is dissolved, as opposed to being dispersed or suspended, within the oil phase. The oil phase may, in turn, be stabilized within the water phase. The oil phase may be such that it is present in discrete droplets or units having an average diameter of about one micron to about 1000 microns, such as from about 1 micron to about 100 microns.

The relative concentrations of water phase and oil phase may be varied. In certain embodiments the percentage by weight of water phase is from about 10% to about 90%, such as from about 40% to about 80%, such as from 50% to about 80%; wherein the balance is oil phase.

The percentage of water included in the compositions may range from about 20% to about 90%, such as from about 20% to about 80%, such as from about 30% to about 70%, such as from about 51% to about 80%, such as from about 51% to about 70%, such as from about 51% to about 60%.

Topical Carrier

The one or more UV-absorbing polymers in the composition may be combined with a "cosmetically-acceptable topical carrier," i.e., a carrier for topical use that is capable of having the other ingredients dispersed or dissolved therein, and possessing acceptable properties rendering it safe to use topically. As such, the composition may further include any of various functional ingredients known in the field of cosmetic chemistry, for example, emollients (including oils and waxes) as well as other ingredients commonly used in personal care compositions, such as humectants, thickeners, opacifiers, fragrances, dyes, solvents for the UV-absorbing polyether, among other functional ingredients. Suitable examples of solvents for the UV-absorbing polyether include dicaprylyl carbonate available as CETIOL CC from Cognis Corporation of Ambler, Pa. In order to provide pleasant aesthetics, in certain embodiments of the invention, the composition is substantially free of volatile solvents, and, in particular, $C_1$-$C_4$ alcohols such as ethanol and isopropanol.

Furthermore, the composition may be essentially free of ingredients that would render the composition unsuitable for topical use. As such, the composition may be essentially free of solvents such as volatile solvents, and, in particular, free of volatile organic solvents such as ketones, xylene, toluene, and the like.

Emulsifiers

The inventors surprisingly have found that UV-protective, mild sunscreens that are substantially free of non-polymeric UV-absorbing sunscreen agents can be made by forming an oil-in-water (O/W) emulsion comprising a polymer composition comprising a UV-absorbing polyether and particular emulsifiers in a particular weight range. As such, compositions of the present invention include an O/W emulsifier component that includes one or more O/W emulsifiers. By "O/W emulsifier," it is meant any of a variety of molecules that are suitable for emulsifying discrete oil-phase droplets in a continuous water phase. By "low molecular weight emulsifiers," it is meant emulsifiers having a molecular weight of about 2000 daltons or less, such as about 1000 daltons or less. The O/W emulsifier may be capable of lowering the surface tension of pure deionized water to 45 dynes per centimeter when added to pure deionized water at a concentration of O/W emulsifier of 0.5% or less at room temperature. O/W emulsifiers are sometimes characterized as having a hydrophile-lipophile balance (HLB) that is about 8 or more, such as about 10 or more.

The O/W emulsifier component comprises one or more anionic emulsifiers, such that the total concentration of anionic emulsifier in the composition is about 3% or less. Examples of suitable chemical classes of anionic emulsifiers are alkyl, aryl or alkylaryl, or acyl-modified versions of the following moieties: sulfates, ether sulfates, monoglyceryl ether sulfates, sulfonates, sulfosuccinates, ether sulfosuccinates, sulfosuccinamates, amidosulfosuccinates, carboxylates, amidoethercarboxylates, succinates, sarcosinates, amino acids, taurates, sulfoacetates, and phosphates. Notable anionic emulsifiers are phosphate esters, such as cetyl phosphate salts, such as potassium cetyl phosphate. In certain embodiments, the concentration of the one or more anionic emulsifiers is from about 0.5% to about 3%, such as from about 0.6% to about 3%, such as from about 0.6% to about 2.5% of the weight of the composition. According to certain embodiments, the O/W emulsifier component consists essentially of the one or more anionic emulsifiers.

According to certain embodiments, the O/W emulsifier component is essentially free of non-ionic emulsifiers having an alcohol-functional group with a hydrocarbon chain length of 14-22 carbon atoms. Chemical classes of non-ionic emulsifiers having an alcohol functional group may include fatty alcohols, such as various saturated or unsaturated, linear or branched, $C_7$-$C_{22}$ unethoxylated, aliphatic alcohols, such as those having a single —OH group. The fatty alcohol may be derived from plant or animal oils and fats having at least one pendant hydrocarbon-comprising chain. The fatty alcohol may have from 14 to about 22 carbon atoms, such as from about 16 to about 18 carbon atoms. Examples of unbranched fatty alcohols include cetyl alcohol and stearyl alcohol.

According to certain other embodiments, the O/W emulsifier component is essentially free of cationic emulsifiers, such as alkyl quaternaries, benzyl quaternaries, ester quaternaries, ethoxylated quaternaries, and alkyl amines.

According to certain embodiments, in addition to the anonic oil-in-water emulsifier(s) discussed above, the O/W emulsifier component includes an additional emulsifier such as a non-ionic emulsifier that is devoid of alcohol functional groups, an amphoteric emulsifier, and/or a polymeric emulsifier. Examples of suitable chemical classes of non-ionic emulsifier include ethoxylates of amides; polyoxyethylene derivatives of polyol esters; noncrosslinked silicone copolymers such as alkoxy or alkyl dimethicone copolyols, silicones having pendant hydrophilic moieties such as linear silicones having pendant polyether groups or polyglycerin groups; and crosslinked elastomeric solid organopolysiloxanes comprising at least one hydrophilic moiety.

Examples of suitable chemical classes of amphoteric emulsifiers include alkyl betaines, amidoalkyl betaines, alkylamphoacetates; amidoalkyl sultaines; amphophosphates; phosphorylated imidazolines; carboxyalkyl alkyl polyamines; alkylimino-dipropionates; alkylamphoglycinates (mono or di); alkylamphoproprionates; N-alkyl β-aminoproprionic acids; and alkylpolyamino carboxylates. Examples of suitable chemical classes of polymeric emulsifier include copolymers based on acrylamidoalkyl sulfonic acid such as Aristoflex® AVC and Aristoflex® HMB by Clariant Corporation; and Granthix APP by Grant Industries, Inc.

Film-Forming Polymers

In certain embodiments of the invention, compositions of the present invention include a film forming polymer. By "film-forming polymer," it is meant a polymer that when dissolved, emulsified, or dispersed in one or more diluents, permits a continuous or semi-continuous film to be formed when it is spread with a liquid vehicle onto smooth glass, and the liquid vehicle is allowed to evaporate. As such, the polymer should dry on the glass in a manner in which over the area which it is spread should be predominantly continuous, rather than forming a plurality of discrete, island-like structures. Generally, the films formed by applying compositions on the skin according to embodiments of the invention described herein, are less than, on average, about 100 microns in thickness, such as less than about 50 microns.

In contrast to polymeric UV-absorbing polymers, film-forming polymers generally do not absorb ultraviolet radiation and therefore do not meet the requirements for UV-absorbing polymers. Film-forming polymers may be useful in compositions of the present invention in that they may enhance the UV-protection (UV-A, UV-B or both) of the composition and/or enhance the waterproofing or water resistance of the composition.

Suitable film-forming polymers include natural polymers such as polysaccharides or proteins and synthetic polymers such as polyesters, polyacrylics, polyurethanes, vinyl polymers, polysulfonates, polyureas, polyoxazolines, and the like. Specific examples of film-forming polymers include, for example, hydrogenated dimer dilinoleyl/dimethylcarbonate copolymer, available from Cognis Corporation of Ambler, Pa. as COSMEDIA DC; copolymer of vinylpyrrolidone and a long-chain a-olefin, such as those commercially available from ISP Specialty Chemicals of Wayne, N.J. as GANEX V220; vinylpyrrolidone/tricontanyl copolymers available as GANEX WP660 also from ISP; water-dispersible polyesters, including sulfopolyesters such those commercially available from Eastman Chemical as EASTMAN AQ 38S. The amount of film-forming polymer present in the composition may be from about 0.1% to about 5%, or from about 0.1% to about 3%, or from about 0.1% to about 2%.

In certain embodiments, the composition includes an emollient used for the prevention or relief of dryness and for the protection of the skin, as well as solubilizing the UV-absorbing polyether. Suitable emollients include mineral oils, petrolatum, vegetable oils (e.g. triglycerides such as caprylic/capric triglyceride), waxes and other mixtures of fatty esters, including but not limited to esters of glycerol (e.g. isopropyl palmitate, isopropyl myristate), and silicone oils such as dimethicone. In certain embodiments, mixtures of triglycerides (e.g. caprylic/capric triclycerides) and esters of glycols (e.g. isopropyl myristate) may be used to solubilize the UV-absorbing polyethers.

In certain embodiments, the composition includes a pigment suitable for providing color or hiding power. The pigment may be one suitable for use in a color cosmetic product, including compositions for application to the hair, nails and/or skin, especially the face. Color cosmetic compositions include, but are not limited to, foundations, concealers, primers, blush, mascara, eyeshadow, eyeliner, lipstick, nail polish and tinted moisturizers.

The pigment suitable for providing color or hiding power may be composed of iron oxides, including red and yellow iron oxides, titanium dioxide, ultramarine and chromium or chromium hydroxide colors, and mixtures thereof. The pigment may be a lake pigment, e.g., an organic dye such as azo, indigoid, triphenylmethane, anthraquinone, and xanthine dyes that are designated as D&C and FD&C blues, browns, greens, oranges, reds, yellows, etc., precipitated onto inert binders such as insoluble salts. Examples of lake pigments include Red #6, Red #7, Yellow #5 and Blue #1. The pigment may be an interference pigment. Examples of interference pigments include those containing mica substrates, bismuth oxychloride substrates, and silica substrates, for instance mica/bismuth oxychloride/iron oxide pigments commercially available as CHROMALITE pigments (BASF), titanium dioxide and/or iron oxides coated onto mica such as commercially available FLAMENCO pigments (BASF), mica/titanium dioxide/iron oxide pigments including commercially available KTZ pigments (Kobo products), CELLINI pearl pigments (BASF), and borosilicate-containing pigments such as REFLECKS pigments (BASF).

The compositions of the present invention may further comprise one or more other cosmetically active agent(s). A "cosmetically active agent" is a compound that has a cosmetic or therapeutic effect on the skin, e.g., agents to treat wrinkles, acne, or to lighten the skin. The cosmetically active agent will typically be present in the composition of the invention in an amount of from about 0.001% to about 20% by weight of the composition, e.g., about 0.01% to about 10% such as about 0.1% to about 5% by weight of the composition.

In certain embodiments the composition has a pH that is from about 4.0 to about 8.0, such as from about 5.5 to about 7.0.

Sun protection factor (SPF) may be tested using the following IN-VITRO SPF TEST METHOD. The baseline transmission of a PMMA plate (substrate) without application of any test materials applied thereto was measured. Test samples were prepared by providing a sample of polymer. Blends may also be tested by this method. The polymer(s) can be tested without any additional additives; with a solvent system, or as a part of a personal care composition that may include solvent and/or additional ingredients.

Each sample is separately applied to a PMMA plate (available from Helioscience, Marseille, France) using an application density of about 32 milligrams for a 25 cm$^2$ substrate, rubbing into a uniform thin layer with the operator's finger, and allowing to dry. The samples are allowed to dry for 15 minutes before measurement of absorbance using calibrated Labsphere® UV-1000S UV transmission analyzer or a Labsphere® UV-2000S UV transmission analyzer (Labsphere, North Sutton, N.H., USA). The absorbance measures were used to calculate SPF and PFA indices (biological protection factor in the UVA based).

SPF and PFA may be calculated using methods known in the art—see equation (1) below for calculation of SPF:

$$SPF_{in\ vitro} = \frac{\int_{\lambda=290\ nm}^{\lambda=400\ nm} E(\lambda) * I(\lambda) * d\lambda}{\int_{\lambda=290\ nm}^{\lambda=400\ nm} E(\lambda) * I(\lambda) * 10^{-A_2(\lambda)} * d\lambda} \quad (1)$$

where:
$E(\lambda)$=Erythema action spectrum
$I(\lambda)$=Spectral irradiance received from the UV source
$A0(\lambda)$=Mean monochromatic absorbance of the test product layer before UV exposure
$d\lambda$=Wavelength step (1 nm)

Compositions of the present invention have low irritation tendencies. Irritation may be measured using, for example, the MODIFIED TEP TEST as set forth below. A lower MODIFIED TEP value of a composition tends to indicate less irritation associated therewith, as compared to a composition having a higher MODIFIED TEP value, which composition tends to cause higher levels of irritation.

Applicants have recognized that compositions of the present invention have surprisingly low MODIFIED TEP values/lower irritation associated therewith. For example, in certain embodiments, the compositions have a MODIFIED TEP value, as determined according to the MODIFIED TEP TEST as set forth below, of 0.3 or less, or about 0.25 or less, or about 0.20 or less.

The compositions of the present invention may be prepared using mixing and blending methodology that is well known by an artisan of ordinary skill. In one embodiment of the invention, a method of making a composition of the present invention includes preparing an oil phase by mixing at least the UV-absorbing polyether with optional oil-soluble or oil-miscible ingredients; and preparing a water phase, by mixing water and optional water-soluble or water-miscible ingredients. The oil phase and the water phase may then be mixed in a manner sufficient to homogeneously disperse the oil phase in the water phase such that the water phase is continuous and the oil phase discontinuous.

The compositions of the present invention can be used by topically administering to a mammal, e.g., by the direct laying on, wiping or spreading of the composition on the skin or hair of a human.

The following MODIFIED TEP TEST is used in the instant methods and in the following Examples. In particular, as described above, the MODIFIED TEP TEST is used to determine when a composition has reduced irritation according to the present invention.

Modified TEP Test:

The MODIFIED TEP TEST is designed to evaluate the ability of a test material to disrupt the permeability barrier formed by a confluent monolayer of Madin-Darby canine kidney (MDCK) cells. MDCK cells grown to confluence on porous filters are used to assess trans-epithelial permeability, as determined by the leakage of fluorescein dye through the monolayer. The MDCK permeability barrier is a model for the outermost layers of the corneal epithelium and this system can therefore be considered to reflect early changes in the development of eye irritation in vivo.

The following equipment is suitable for the MODIFIED TEP TEST: Packard Multiprobe 104 Liquid handling system; BioTek Washer, model number ELx405; and BioTek Powerwave XS microplate reader with a 490 nm filter. Disposable lab ware includes: Corning Support Transwell 24-well cell culture plate with microporous membrane, Cat. No. 29445-100 or 29444-580, MFG. No. 3397; Corning Receiver 24-well Tissue Culture Plate, Cat No. 29444-100, MFG. No. 3527; disposable 200 µL tips Cat. No. 82003-196; Eppendorf 5 mL combitips plus Cat No. 21516-152; Sodium Chloride 0.9% (w/v) Aqueous Cat. No. RC72105; and sterile 15 mL polypropylene centrifuge tubes. Reagents supplied by Life Technologies include: Hank's Balanced Salt Solution (10×) without Phenol Red Cat. No. 14065056 and Sodium Bicarbonate Solution, 7.5% Cat No. 25080094, Minimum Essential Medium (MEM) (1×), Cat No. 11095072, Fetal Bovine Serum, HI Cat No. 10082147, Antibiotic Antimycotic 100× Cat No. 15240096, L-Glutamine 200 mM (100×) Cat No. 25030081, Sodium Fluorescein, Sigma Cat. No. F-6377 is provided by Sigma/Aldrich.

A cell line, ATCC CCL 34 MDCK (NBL-2) (Kidney: Canis familiaris), is maintained in accordance ATCC (Manassas, Va.) recommendations. Cell cultures are harvested by trypsinization and seeded into Support Transwell24 plates containing complete MEM, 48 hours prior to testing at a concentration of $5 \times 10^5$ cells per mL. Reagents are prepared: (1) 1× HBSS Buffer by combining 200 mL Hank's Balanced Salt Solution (HBSS) (10×) without phenol red with 9.3 mL Sodium Bicarbonate and increasing the volume to 2000 mL with distilled water. The pH should be in the range of 6.8-7.2 and the solution should be warmed to 37 C; (2) a 200 ug/mL stock solution of sodium fluorescein in HBSS Buffer; (3) Complete Minimum Essential Medium (MEM) is prepared by combining 100 mL's of Fetal Bovine Serum, 10 mL's of Antibiotic Antimycotic 100×, and 10 mL's of L-Glutamine 200 mM (100×) to 1000 mL's of MEM (1×).

Permeability of the membrane is confirmed by including a No Cell Control that is run with each day of testing. Sunscreen test compositions are evaluated full strength.

Inserts are washed to remove cell medium. A 24-well cell culture plate, Corning Cat No. 29445-100, containing a confluent monolayer of MDCK cells is removed from the incubator. Each 24-well cell culture plate includes an insert which holds an inner well with a microporous membrane cell growth surface suspended into a lower well. The insert containing the cell cultures is washed 5× (BioTek Washer) with warm HBSS to remove culture medium and serum. The bottom portion of the 24-well cell culture plate is washed with warm HBSS 3× and on the last wash 1 mL of HBSS is dispensed in each bottom well.

Four wells in the 24-well plate are used per sunscreen test composition, so a single 24-well plate can be used to test up to 6 sunscreen test compositions. The sunscreen test compositions are added directly to the insert well, Neat (100%), 200 µL per insert well. The 24-well cell culture plate is then returned to the incubator for a 1 hour incubation period.

Upon completion of the first incubation step, the 24-well cell culture plate is removed from the incubator and washed manually to remove test composition. Approximately 200 µL of HBSS is added to each inner well and allowed to soak for approximately 1 minute. The test composition and HBSS are then decanted from the individual wells. Any residual sample is removed by delicately flooding the inserts with HBSS and decanting. When the insert is free of residual test composition, a 10× wash (Bio Tek Washer) with warm HBSS should be done. The bottom wells are washed with warm HBSS 3× and on the last wash 1 mL of HBSS (receiver buffer) is dispensed into each bottom well.

The insert is placed back into the bottom plate containing 1 mL HBSS (receiver buffer), sodium fluorescein is added to each inner well, 200 µL per well, and the plate is returned to the incubator for a period of 45 minutes.

After the 45 minute incubation, the sodium fluorescein containing first plate is removed from the incubator, the upper insert is removed, and the amount of dye that has leaked into the receiver buffer in the lower well is determined by the Powerwave XS microplate reader. The fluorescence is read spectrophotometrically at 490 nm. Data are printed and recorded.

The insert is then placed into an empty, temporary, 24 well bottom plate on the Bio Tek Washer for a 10× HBSS wash. Care is taken to ensure that the sodium fluorescein has been washed off and there is no residual fluorescein in the top (inner) or bottom wells.

The washed insert is placed into a fresh 24-well receiver cell culture plate, Corning Cat No. 29445-100. Both the inner wells of the insert and the bottom plate receive complete minimum essential medium (MEM), Life Technologies, Cat No. 11095072. Approximately 1 mL of complete MEM is added to the bottom wells and 200 µL is added to the inner wells. The 24-well cell culture plate is then incubated for 3 hours.

After the 3 hour incubation the 24-well cell culture plate is removed from the incubator. The insert containing the cell cultures is washed 5× (BioTek Washer) with warm HBSS to remove culture medium and serum. The bottom plate is washed with warm HBSS 3× and on the last wash 1 mL of HBSS is dispensed in each bottom well (receiver buffer).

Sodium fluorescein is added to each inner insert well, 200 µL per well, and the plate is reassembled and returned to the incubator for a period of 45 minutes.

After the 45 minute incubation, the sodium fluorescein containing plate is removed from the incubator, the insert is removed and discarded, and the amount of dye that has leaked into the lower well is determined by the Powerwave XS microplate reader. The fluorescence is read spectrophotometrically at 490 nm. Data is printed and recorded.

The spectrophotometric measurement (fluorescein leakage) value for each of the four repeats of a given sunscreen test composition is used to calculate an average fluorescein leakage value for the sunscreen test composition. The average fluorescein leakage value of the four "no cell control" wells is also calculated. The Modified TEP Score is calculated by dividing the average fluorescein leakage value of the sunscreen test composition by that of the no cell control.

Additional details of the TEP test are described in the following publication: Tchao, R. (1988) Trans-epithelial Permeability of Fluorescein In Vitro as an Assay to Determine Eye Irritants. Alternative Methods in Toxicology 6, Progress in In Vitro Toxicology (ed. A. M. Goldberg), 271.

The following examples are illustrative of the principles and practice of this invention, although not limited thereto. Numerous additional embodiments within the scope and spirit of the invention will become apparent to those skilled in the art once having the benefit of this disclosure.

EXAMPLES

Examples 1-12: Synthesis and SPF Testing of Polymer Compositions Comprising UV-Absorbing Polyethers Example 1. Synthesis of a Protected Form of Glycidol

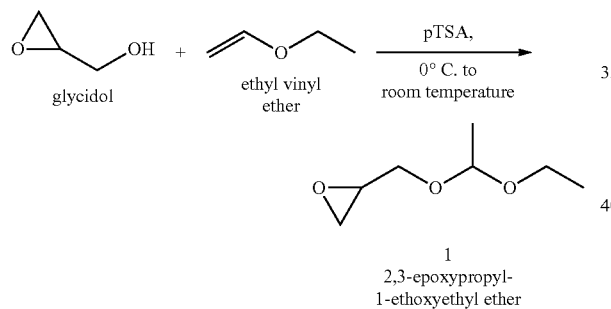

Formula VIII. Synthesis of Protected Epoxide Monomer

The synthesis of protected epoxide monomer 1 was performed as illustrated in FORMULA VIII using a variation of a procedure described in the literature (Fitton, A. et. al. *Synthesis* 1987, 1987, 1140-1142). Glycidol (53 mL, 0.80 moles) and ethyl vinyl ether (230 mL, 2.40 moles; distilled immediately before reaction) were added to a 2-neck 500 mL round bottom flask containing a magnetic stir bar. The flask was fitted with a septum and thermometer adapter; a thermometer was inserted into the adapter and positioned such that the bulb was immersed in the liquid. The flask was immersed in a brine/ice bath; the mixture was magnetically stirred. When the internal temperature was 0° C., p-toluene sulfonic acid hydrate (pTSA·$H_2O$, 1.43 g, 7.5 mmol) was added in small portions while stirring vigorously. On addition of each portion of pTSA, the temperature of the solution increased sharply; the rate of addition was slow enough to prevent the solution temperature increasing above 20° C. The final portion of pTSA was added ~5 hours after addition of the initial portion, and resulted in no exotherm; thin layer chromatography of the reaction mixture revealed no residual glycidol following the final pTSA addition. The reaction mixture was transferred into a separatory funnel; saturated aqueous $NaHCO_3$ (230 mL) was poured into the funnel slowly. The mixture was shaken, the layers allowed to separate, and the organic layer was removed, dried over sodium sulfate, and filtered through paper. The solution was concentrated by rotary evaporation, then vacuum distilled (60° C. distillate at 8 torr) affording protected epoxide monomer 1 (79.38 g) as a clear oil. NMR analysis was performed on a Varian Unity Inova 400 MHz spectrometer ($^1$H) spectrometer at 30° C.; chemical shifts are reported in parts per million (ppm) on the δ scale, and were referenced to residual protonated solvent peaks or tetramethylsilane. Spectra obtained in DMSO-$d_6$ were referenced to ($CHD_2$)($CD_3$)SO at $δ_H$ 2.50. $^1$H NMR (400 MHz, $CDCl_3$) δ ppm 4.76 (quin, J=5.2 Hz, 1H), 3.81 (dd, J=11.5, 3.3 Hz, 1H), 3.60-3.74 (m, 3H), 3.38-3.60 (m, 4H), 3.10-3.20 (m, 2H), 2.81 (ddd, J=5.1, 4.0, 1.3 Hz, 2H), 2.63 (ddd, J=14.6, 5.1, 2.7 Hz, 2H), 1.33 (dd, 5.4 Hz, 6H), 1.21 (td, J=7.1, 1.3 Hz, 6H).

Example 2A. Synthesis of Linear Polyglycerol

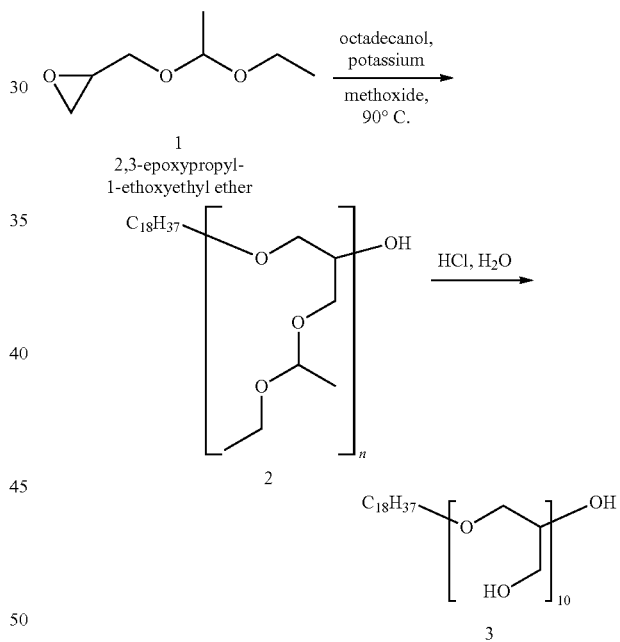

Formula IX. Synthesis of Linear Polyether Polymer

Polymerization of protected epoxide monomer 1 was achieved as illustrated in FORMULA IX. 1-Octadecanol (27.76 g, 102.6 mmol) was added to an oven-dried 250 mL 2-neck round bottom flask containing a magnetic stir bar. The flask was fitted with a nitrogen inlet adapter and rubber septum. Potassium methoxide (25 wt % in methanol (MeOH), 6.06 mL, 20.52 mmol) was added to the flask by syringe through the septum. The round bottom flask was immersed in an oil bath which had been pre-heated to 90° C. The septum was pierced with an 18 gauge needle, and the material in the flask was stirred under a constant stream of nitrogen gas for 1 hour, during which time the alcohol melted, and methanol evaporated from the flask. The septum was replaced with a pressure equalizing addition funnel containing monomer 1 (151 g, 1.04 moles). The funnel was sealed with a rubber septum. The monomer 1 was added dropwise to the stirred mixture; the reaction mixture was stirred at 90° C. for 15 hours. On cooling, this afforded crude polyether 2 as a pale brown, slightly viscous oil that was used in subsequent reactions without further purification. $^1$H NMR (400 MHz, CHLOROFORM-d) δ ppm 4.48-4.80 (m, 10H), 3.25-3.97 (m, 70H), 1.41-1.64 (m, 2H), 1.23-1.40 (m, 60H), 1.09-1.23 (m, 30H), 0.88 (t, J=7.0 Hz, 3H).

Gel permeation chromatography for molecular weight determination was performed at 35° C. on a Waters Alliance 2695 Separations Module (Waters, Milford, Mass.) at a flow rate of 0.5 mL/min THF (stabilized w/0.025% BHT). The 2695 was equipped with two GPC columns in series (Waters Corp HR 0.5 and HR3) with dimensions of 7.8×300 mm with 5 μm particle size) and a Waters model 410 refractive index detector. The molecular weights of the samples were determined by comparison to polystyrene standards. Standards were prepared by weighing 1-2 mg of each polystyrene (PS) polymer into a 2 mL vial with THF solvent (2 standards per vial); samples were filtered (0.22 μm) prior to analysis. Polystyrene standards spanned a range between 70,000 to 600 Daltons, and were manufactured by three vendors (Polymer Standards Service-USA, Phenomenex and Shodex). The resultant calibration curve provided an $r^2$=0.9999. Experimental samples were dissolved in THF at a concentration of 3-5 mg/mL and filtered (0.22 μm) prior to analysis. GPC (THF) analysis for polymer 2: $M_w$ 1724.

Crude polyether 2 was transferred with tetrahydrofuran (THF, ~500 mL) into a 1 L round bottom flask containing a magnetic stir bar. Concentrated aqueous HCl (37%, 20 mL) was added to the stirred reaction mixture by glass pipette. After 16 hours, the reaction mixture was concentrated by rotary evaporation to an oil which was diluted with methanol to ~500 mL. Solid NaHCO$_3$ was added in portions to the vigorously stirred solution, causing significant bubbling. When addition of the NaHCO$_3$ did not produce further bubbling (total NaHCO$_3$ added was 107 g) the mixture was filtered through paper to remove solid NaHCO$_3$. The filtrate was concentrated by rotary evaporation affording linear polyglycerol 3 as a tan foam. $^1$H NMR (400 MHz, DMSO-d$_6$) δ ppm 4.43 (br. s., 11H), 3.20-3.70 (m, 52H), 1.38-1.55 (m, 2H), 1.23 (s, 30H), 0.85 (t, J=7.0 Hz, 3H).

Example 2B. Synthesis of Linear Polyglycerol

A different batch of protected crude polymer 2 (260 g) and methanol (ACS grade, 1.25 L) was transferred into a 2 L 2-neck round bottom flask. Dry, H$^+$ form acidic ion-exchange resin in (Dowex DR-2030 from Aldrich, 446483; 100.3 g) was added to the flask. The center neck of the flask was fitted with an adapter for mechanical stirring and a paddle; the side neck of the flask was fitted with a water cooled distillation adapter. The reaction flask was immersed in an oil bath. With vigorous mechanical stirring, the reaction mixture was heated to boiling (oil bath temperature of 85° C.). Methanol (and the methyl ether resulting from removal of the protecting groups) was distilled from the flask. After 750 mL of methanol were collected, an additional portion of methanol (750 mL) was added to the reaction mixture. Another 750 mL of methanol was allowed to distill from the flask. Decolorizing charcoal was added to the hot reaction mixture. The mixture was stirred briefly and then filtered through paper. The filtrate was concentrated by rotary evaporation. Residual solvent was removed under vacuum affording the final linear polyglycerol as a yellowish foam (107 g).

Example 3A. Synthesis of Benzotriazole Chromophore Carboxylate

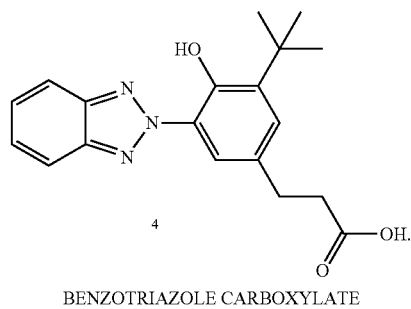

FORMULA X

BENZOTRIAZOLE CARBOXYLATE

The polyethylene glycol ester of 3-[3-(2H-1,2,3-benzotriazol-2-yl)-5-tert-butyl-4-hydroxyphenyl]propanoate (a chromophore sold under the trade name TINUVIN 213 by BASF Corporation, Wyandotte, Mich.) (81.0 g) was added to a 2 L round bottom flask containing a magnetic stir bar. EtOH (600 mL) was added to the flask by funnel, and the mixture was stirred until homogeneous. Sodium hydroxide (NaOH, 30.8 g) was dissolved in H$_2$O (400 mL); the basic solution was transferred into an addition funnel above the 2 L flask. The NaOH solution was added slowly to the stirred mixture; the pale amber cloudy solution immediately turned clear and dark orange. When addition was complete, the mixture was stirred overnight at room temperature. The solution was concentrated by rotary evaporation to remove most of the EtOH. The resulting orange oil was diluted to 1400 mL with H$_2$O. The mixture was stirred mechanically and was acidified to ~pH 1 by addition of 1 M aq. HCl (~700 mL). The resulting white precipitate was filtered and pressed to remove water, then recrystallized from EtOH. The first crop of crystals were long, thin colorless needles. The supernatant was removed and concentrated by rotary evaporation; a second crop of material was isolated as a white, amorphous solid. The two crops were combined and dried in a vacuum oven overnight affording a UV-chromophore having a carboxylate group, specifically benzotriazole carboxylate 4, 3-(3-(2H-benzo[d][1,2,3]triazol-2-yl)-5-(tert-butyl)-4-hydroxyphenyl)propanoic acid (37.2 g) as a white solid; the structure is illustrated in FORMULA X. $^1$H NMR (400 MHz, DMSO-d$_6$) δ ppm 11.25 (br. s, 1H), 8.00-8.20 (m, 2H), 7.95 (d, J=2.1 Hz, 1H), 7.50-7.67 (m, 2H), 7.28 (d, J=2.1 Hz, 1H), 2.87 (t, J=7.5 Hz, 2H), 2.56 (t, J=7.5 Hz, 2H), 1.45 (s, 9H).

Example 3B. Synthesis of Benzotriazole Chromophore Carboxylate

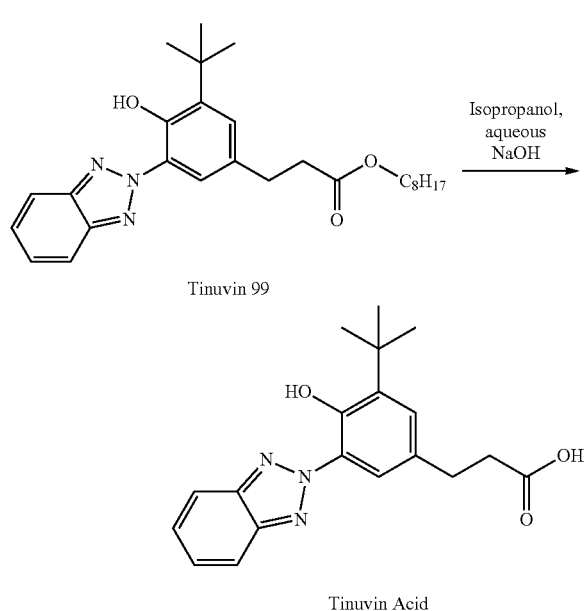

Tinuvin 99

Tinuvin Acid

Benzenepropanoic acid, 3-(2H-benzotriazol-2-yl)-5-(1,1-dimethylethyl)-4-hydroxy-, C7-9-branched and linear alkyl esters, commercially available as TINUVIN 99 from BASF (120 g, 265.7 mmol) was added to a 3 L single neck round bottom flask containing a magnetic stir bar. Isopropanol (900 ml, ACS grade) was added to the flask, and the resulting mixture was stirred until complete dissolution. Sodium hydroxide (36 g, 900 mmol) was dissolved in 600 ml of distilled water, and the solution was added to the reaction mixture. The resulting opaque mixture, which in 40 min became a clear orange solution, was stirred at room temperature for 24 hours, and then slowly added to a vigorously stirred mixture of isopropanol (1800 ml, ACS grade) and 1N HCl (1200 ml), cooled to 10-15° C. The precipitated white solid was filtered, washed with 1.2 L of 1:1 isopropanol-1N HCl mixture, suspended in 2 L of 0.25N HCl, stirred for 1 hour, filtered and dried at 90° C. in a vacuum oven overnight. The resulting UV-chromophore having a carboxylate group, specifically a benzotriazole carboxylate 4 (37.2 g) was obtained as a pale yellow solid, 85 g, 94.5%.

Example 4. Esterification of Polyether Backbone with Benzotriazole Carboxylate

FORMULA XI. ESTERIFICATION OF POLYGLYCEROL WITH BENZOTRIAZOLE CARBOXYLATE

FORMULA XI illustrates the esterification of polyglycerol 3 with benzotriazole carboxylate 4 using catalytic tin. Linear polyglycerol 3 of Example 2A (5.52 g, 60.1 hydroxyl milliequivalents) was dissolved in methanol and transferred into a 500 mL 2-neck round bottom flask. The methanol was removed using rotary evaporation; benzotriazole carboxylate 4 (20.38 g, 60.1 mmol)) and a magnetic stir bar were added to the flask. The flask was fitted with a nitrogen inlet adapter and vacuum distillation adapter with 100 mL receiving flask. The flask was placed under vacuum (<1 Torr) for 1 hour, then backfilled with nitrogen gas. The inlet adapter was removed from the 500 mL flask; tin (II) ethyl hexanoate (49 μL, 0.15 mmol) was added to the flask by syringe under a stream of nitrogen. The apparatus was reassembled and immersed in an oil bath pre-heated to 200° C. When most of the solid had melted, the oil bath was cooled to 190° C. The reaction was stirred under a flow of nitrogen for 16 hours. While maintaining temperature and stirring, the reaction flask was then placed under vacuum (<1 Torr) for an additional 24 hours. The apparatus was then backfilled with nitrogen and cooled to room temperature. The material was freeze fractured and ground to powder using a mortar and pestle. The powder was dissolved in a minimal amount of THF. Methanol (900 mL) and a magnetic stir bar were added to an Erlenmeyer flask; the flask was immersed in an ice bath. The THF solution was added to the methanol with vigorous stirring; the resulting precipitate was isolated by vacuum filtration. Residual solvent was removed under vacuum overnight, affording the linear polyglycerol 5 (18.7 g) as an off-white solid. $^1$H NMR (400 MHz, CDCl$_3$) δ ppm 11.71 (br. s., 9H), 8.03 (br. s., 9H), 7.80 (br. s, 18H), 7.28-7.48 (m, 18H), 7.12 (br. s, 9H), 5.19 (br. s, 1H), 3.98-4.46 (br. m, 20H), 3.21-3.61 (br. m, 32H), 2.91 (br. s, 18H), 2.67 (br. s, 18H), 1.38-1.51 (m, 85H), 1.13-1.35 (m, 28H), 0.87 (t, J=6.6 Hz, 3H). GPC (THF): $M_w$ 3299; $M_n$ 2913.

Example 5. Conversion of Benzotriazole Carboxylate to Acid Chloride (3-(3-(2H-benzo[d][1,2,3]triazol-2-yl)-5-(tert-butyl)-4-hydroxyphenyl)propanoyl chloride)

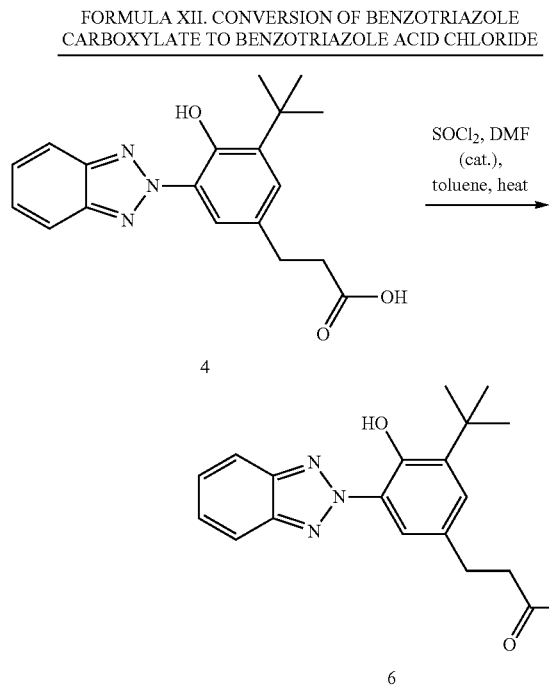

FORMULA XII. CONVERSION OF BENZOTRIAZOLE CARBOXYLATE TO BENZOTRIAZOLE ACID CHLORIDE

The conversion of the benzotriazole carboxylic acid 4 to the corresponding benzotriazole acid chloride 6 is illustrated in FORMULA XII. Benzotriazole carboxylate 4 (50 g 147 mmol, synthesized as described in Example 3 was added to a 1000 mL 3-neck flask containing a magnetic stir bar; the flask was equipped with a reflux condenser, nitrogen inlet, and rubber septum. Anhydrous toluene (~500 mL) was transferred into the flask by cannula through the septum. Thionyl chloride (16.1 mL, 221 mmol) was transferred into the flask by syringe; dimethylformamide (2.7 mL) was then added to the flask by syringe. The flask was immersed in an oil bath set at 80° C.; the suspension was stirred; the solids began to disperse, eventually yielding a clear solution. After ~4 hours, the reaction mixture was allowed to cool, transferred to a round bottom flask and concentrated by rotary evaporation. The resulting oil was triturated with hexanes, affording a beige solid. The suspension of material was recrystallized by adding additional hexanes and warming to reflux, filtration through paper, and slow cooling to room temperature with stirring. The resulting beige crystals were filtered and dried under vacuum at 50° C. The filtrate was concentrated, and the recrystallization performed a second time affording a second crop of crystals; the mass of the combined crops of benzotriazole acid chloride 6 was 44.7 grams. $^1$H NMR (400 MHz, CDCl$_3$) δ 11.88 (s, 1H), 8.16 (d, J=2.2 Hz, 1H), 7.91-7.98 (m, 2H), 7.47-7.54 (m, 2H), 7.21 (d, J=2.2 Hz, 1H), 3.29 (t, J=7.5 Hz, 2H), 3.07 (t, J=7.5 Hz, 2H), 1.50-1.53 (s, 9H).

Example 6. Conversion of Benzotriazole Acid Chloride to Isocyanate (2-(2H-benzo[d][1,2,3]triazol-2-yl)-6-(tert-butyl)-4-(2-isocyanatoethyl)phenol)

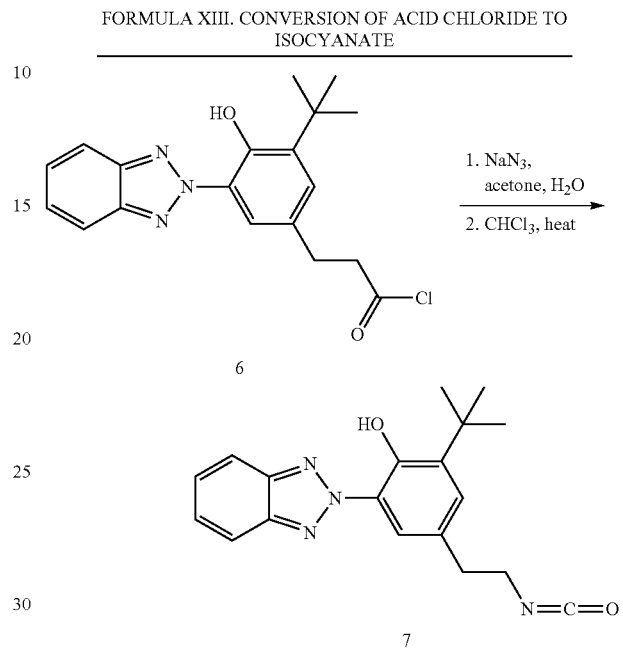

FORMULA XIII. CONVERSION OF ACID CHLORIDE TO ISOCYANATE

Synthesis of a benzotriazole isocyanate 7 suitable for coupling to pendant functional groups is illustrated in FORMULA XIII Sodium azide (NaN$_3$, 2.5 g, 38 mmol: CAUTION! NaN$_3$ is a violent poison) was carefully transferred into a single necked 500 mL round bottom flask containing a magnetic stir bar. Deionized water (20 mL) was added to the flask; the NaN$_3$ dissolved with mixing affording a clear solution. The flask was immersed in an ice bath. Acid chloride 6 (7.0 g 20 mmol) and anhydrous acetone (45 mL) were transferred into a pressure equalizing addition funnel in a positive pressure N$_2$ atmosphere glove box. The acid chloride dissolved in the acetone with gentle swirling, affording a clear yellow solution. The addition funnel containing benzotriazole acid chloride 6 was fitted into the flask containing the aqueous solution of NaN$_3$; the top of the addition funnel was fitted with a N$_2$ adapter connected to a vacuum gas manifold. The solution of benzotriazole acid chloride 6 was added dropwise to the NaN$_3$ solution. After addition of several drops, a white precipitate began to appear, suspended in the aqueous solution. Addition of benzotriazole acid chloride 6 was complete within 30 minutes; mixing was continued for 20 minutes in the ice bath. Water (30 mL) was added to the resulting white slurry; solids were collected by filtration through a glass fritted funnel under vacuum. The white solid was transferred to a separatory funnel followed with CHCl$_3$ (185 mL). The flask was shaken and the layers were allowed to separate. The lower organic phase was removed from the small aqueous layer and dried over Na$_2$SO$_4$. The solution was filtered; the filtrate was placed in a single necked 500 mL round bottom flask containing a magnetic stir bar; the flask was fitted with a reflux condenser with nitrogen inlet adapter and immersed in an oil bath. The solution was heated slowly to reflux over 30 minutes. The final oil bath temperature was 65° C. As the oil bath temperature surpassed 55° C., bubbling was apparent in the solution. The reaction was allowed to reflux for a total of 90 min. CHCl$_3$ was then removed by rotary evaporation; the resulting oil crystallized overnight on standing affording the benzotriazole isocyanate 7 (5.8 g) as a slightly grey solid. $^1$H NMR (400 MHz, CDCl$_3$) δ 11.91 (s, 1H), 8.18 (d, J=1.9 Hz, 1H), 7.92-7.98 (m, 2H), 7.47-7.53 (m, 2H), 7.23 (d, J=2.1 Hz, 1H), 3.59 (t, J=6.9 Hz, 2H), 2.96 (t, J=6.9 Hz, 2H), 1.52 (s, 9H).

Example 7. Coupling of Isocyanate to Polyglycerol

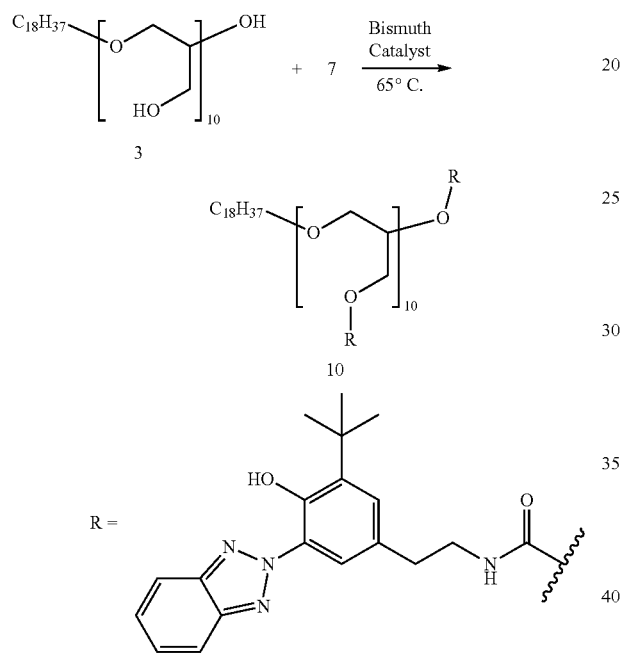

The reaction of linear polyglycerol 3 with benzotriazole isocyanate 7 is illustrated in FORMULA XIV.

A solution of polyglycerol 3 in methanol was concentrated by rotary evaporation; residual solvent was removed in a vacuum oven overnight at 75° C. The polymer (2.22 g, 24.1 hydroxyl milliequivalents) was added to a 100 mL 2-neck round bottom flask containing a magnetic stir bar. Isocyanate 7 (7.65 g, 22.7 mmol), bismuth catalyst (25 mg; a bismuth carboxylate complex sold under the trade name BICAT 8210 by Shepherd Chemical, Norwood, Ohio) and THF (17.4 ml, dried over 3 angstrom molecular sieves) were added to the flask. The flask was placed in a 65° C. heated oil bath and fitted with a gas inlet. The reaction mixture was stirred for 5 hours under a nitrogen atmosphere, then allowed to cool to room temperature. FTIR was used to confirm the disappearance of the strong isocyanate peak at 2250 cm$^{-1}$. The reaction mixture was poured into 160 ml of methanol, resulting in a tan precipitate. Methanol was decanted off and the product was washed in the flask with methanol (2×75 mL). Residual solvent was removed in a vacuum oven overnight at 60° C.; the material was ground to a fine powder.

Example 8. Synthesis of an Epoxide Chromophore for the Direct Polymerization Method

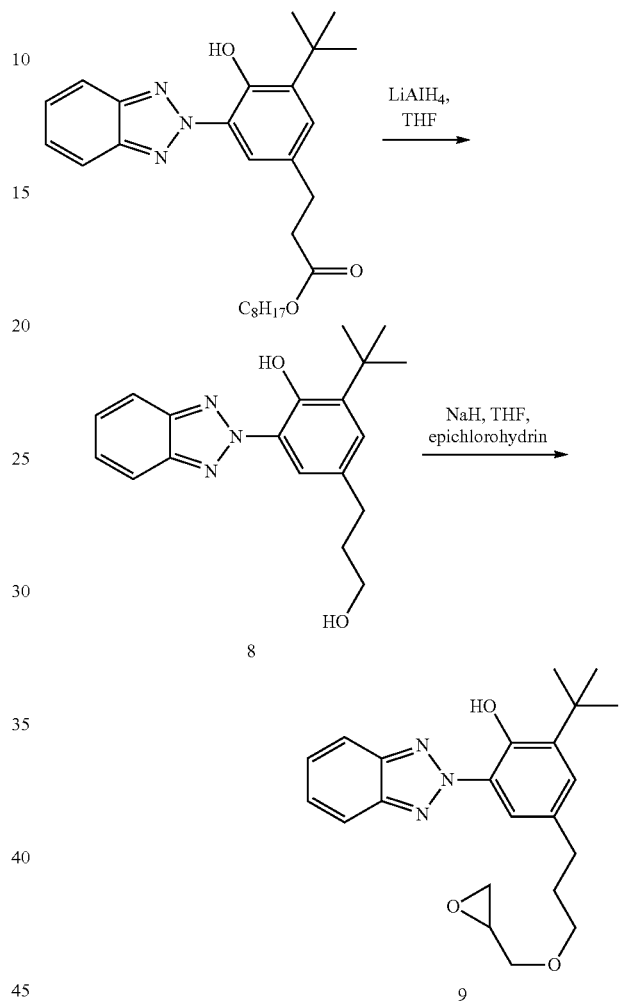

The synthesis of an epoxide monomer 9 bearing a benzotriazole chromophore is illustrated in FORMULA XV. A solution of lithium aluminum hydride (LAH) in THF (a 1 M, 250 mL) was transferred by cannula under nitrogen atmosphere into an oven-dried 500 mL 2-neck round bottom flask containing a magnetic stir bar and fitted with a rubber septum and pressure equalizing addition funnel. The reaction flask was immersed in an ice bath; stirring was started. Benzenepropanoic acid, 3-(2H-benzotriazol-2-yl)-5-(1,1-dimethylethyl)-4-hydroxy, C7-C9 branched and linear alkyl ester containing 5 wt. % 1-methoxy-2-propyl acetate (50.06 g; a benzotriazole UV absorbing product sold under the trade name TINUVIN 99-2 by BASF Corporation, Wyandotte, Mich.) was transferred into the addition funnel, and dissolved in anhydrous THF (30 mL). The THF solution containing the benzotriazole was added dropwise to the solution containing LAH; this resulted in slow fizzing. After the addition was complete, an additional portion of LAH solution (100 mL) was cannulated into the reaction flask. The reaction was allowed to warm to room temperature with stirring. After 2 hours, the reaction mixture was poured into a 1 liter erlenmeyer flask which was immersed in an ice bath. The solution was stirred mechanically while water (~60 mL) was added slowly to quench any residual LAH (EXTREME CAUTION: quenching of LAH with water is exothermic and releases large quantities of highly flammable $H_2$ gas). When the LAH was quenched (no additional gas released with additional water), the grey suspension was diluted to 1 L with 1 M aqueous HCl. This solution was transferred into a 2 L separatory funnel and extracted with ethyl acetate (1×400 mL, then 2×50 mL). The combined ethyl acetate layers were washed with brine (1×400 mL), dried over $Na_2SO_4$, then filtered through paper. Solvent was removed first by rotary evaporation and then in a vacuum oven overnight affording benzotriazol alcohol 8 (42.16 g) as a beige solid with a strong unpleasant odor. $^1$H NMR (400 MHz, CDCl$_3$) δ ppm 11.75 (s, 1H), 8.15 (d, J=2.1 Hz, 1H), 7.88-7.99 (m, 2H), 7.43-7.52 (m, 2H), 7.22 (d, J=2.1 Hz, 1H), 3.75 (m, 2H), 3.62 (br. s, 1H), 2.77 (t, J=7.7 Hz, 2H), 1.91-2.06 (m, 2H), 1.52 (s, 9H).

Sodium hydride (6.0 g, 250 mmol) was added to an oven-dried 3-neck round bottom flask containing a magnetic stirring bar. The flask was fitted with a pressure equalizing addition funnel, nitrogen inlet adapter and rubber septum. Anhydrous THF (300 mL) was added to the flask by cannula under nitrogen; the flask was then immersed in an ice bath, and stirring was starting. Benzotriazol Alcohol 8 (20.0 g, 61.5 mmol) and a small magnetic stirring bar were added to the addition funnel; THF was cannulated into the addition funnel, and the stir bar was agitated to promote dissolution of the alcohol in the THF. The final volume of the alcohol/THF solution was 65 mL. This solution was added dropwise to the cold, stirred sodium hydride suspension. The cold reaction mixture was stirred for 1 hour, then epichlorohydrin (20 mL, 256 mmol) was added by syringe through the septum. The addition funnel was exchanged with a reflux condenser with nitrogen inlet, and the round bottom flask was immersed in an oil bath at 70° C. The mixture was stirred for 19 hours, then the mixture was transferred to a separatory funnel with 1M aqueous HCl (750 mL) and ethyl acetate (500 mL). After shaking, the aqueous layer was discarded. The organic layer was washed with water (2×250 mL) and brine (1×250 mL) then dried over $Na_2SO_4$. The solution was concentrated by rotary evaporation. The crude product was purified by chromatography on silica gel (6:1 hexanes/ethyl acetate). Fractions containing the desired product were pooled, concentrated by rotary evaporation; residual solvent was removed under vacuum overnight affording the epoxide monomer 9 bearing a benzotriazole chromophore (7.35 g) as a beige solid. $^1$H NMR (400 MHz, CDCl$_3$) δ ppm 11.77 (s, 1H), 8.14 (d, J=1.9 Hz, 1H), 7.85-8.00 (m, 2H), 7.41-7.53 (m, 2H), 7.21 (d, J=1.9 Hz, 1H), 3.74 (dd, J=11.5, 3.1 Hz, 1H), 3.57 (ddt, J=19.8, 9.3, 6.4 Hz, 2H), 3.43 (dd, J=11.5, 5.8 Hz, 1H), 3.19 (ddt, J=5.8, 4.0, 2.9 Hz, 1H), 2.82 (br. t, J=4.7 Hz, 1H), 2.76 (br. t, J=7.7 Hz, 2H), 2.64 (dd, J=5.1, 2.6 Hz, 1H), 1.93-2.04 (m, 2H), 1.52 (s, 9H).

Example 9. Esterification of Alternate Polyglycerol with Benzotriazole Acid

A polyglycerol partially esterified with stearic acid (2.5 g, 19.8 hydroxy milliequivalents; tetradecaglyceryl monostearate sold under the trade name POLYALDO 14-1-S by Lonza, Allendale, N.J.) and benzotriazole carboxylate 4 (8.8 g, 23.8 mmol) were transferred into a 2-neck 100 mL round bottom flask containing a magnetic stir bar. The flask was fitted with a nitrogen inlet adapter and distillation adapter with 100 mL receiving flask. The apparatus was placed under vacuum for one hour, then backfilled with nitrogen. The distillation head was removed, and tin (II) ethyl hexanoate (50 μL) was added to the reaction flask by syringe under nitrogen flow. The apparatus was reassembled, then purged under vacuum and backfilled with nitrogen 3 times. The reaction flask was immersed in an oil bath that was warmed to 180° C. with constant flow of nitrogen into the 2-neck flask through the distillation adapter and out of the vacuum adapter to room atmosphere. The reaction was stirred for three hours and then cooled to room temperature under nitrogen flow, affording the product, a UV-absorbing polyglycerol, as a yellow solid. $^1$H NMR (400 MHz, CDCl$_3$) δ ppm 11.81 (br. s., 2H), 8.15 (br. s., 2H), 7.75-8.02 (br. s, 4H), 7.34-7.58 (br. s, 4H), 7.21 (br. s., 2H), 4.93-5.32 (br, 1H), 3.17-4.50 (br. m, 38H), 2.86-3.11 (br. m, 4H), 2.54-2.84 (br. m, 4H), 2.31 (br. s., 2H), 1.61 (br. s., 2H), 1.50 (br. s., 18H), 1.26 (br. s., 28H), 0.89 (t, J=6.3 Hz, 3H). GPC (THF): $M_w$ 1700; $M_n$ 950.

Example 10. Synthesis of Benzotriazole Acid Methyl Ester

FORMULA XVI. SYNTHESIS OF METHYL ESTER 11

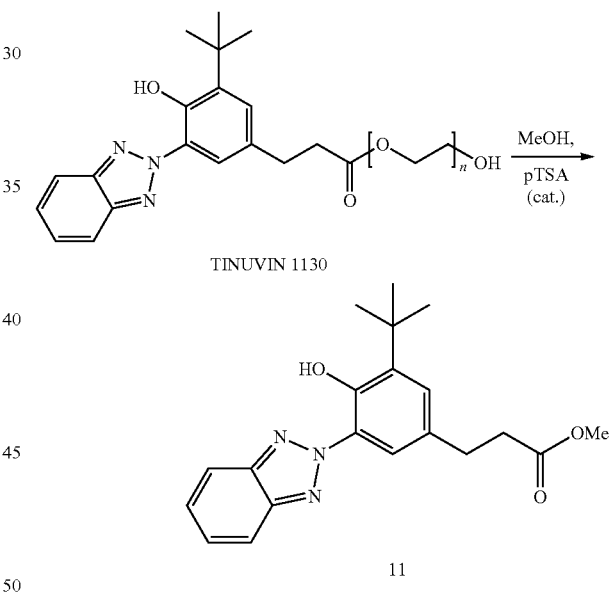

The synthesis of benzotriazole methyl ester 11 intended for transesterification with a polymer with hydroxyl functional groups is illustrated in FORMULA XVI. Beta-[3-(2-H-benzotriazole-2-yl)-4-hydroxy-5-tert-butylphenyl]-propionic acid-poly(ethylene glycol) 300-ester (50.1 g; a UV absorbing product sold under the trade name TINUVIN 1130 by BASF Corporation, Wyandotte, Mich.) was added to a 2-neck 1 liter round bottom flask containing a magnetic stir bar. Methanol (500 mL) was added to the flask. The flask was immersed in an oil bath; the solution was stirred. p-TSA.H$_2$O (0.63 g) was added to the solution. The 2-neck flask was fitted with a reflux condenser and rubber septum; the stirred reaction mixture was brought to reflux by warming the oil bath; reflux was maintained for 17 hours. The flask was then removed from the oil bath and allowed to cool to room temperature, whereupon the product precipitated as a white solid. The precipitate was isolated by vacuum filtration, and then recrystallized from methanol; the solids were isolated by vacuum filtration and dried under vacuum at 80° C. affording the benzotriazole methyl ester 11 (18.27 g) as a white solid. $^1$H NMR (400 MHz, CDCl$_3$) δ ppm 11.81 (s, 1H), 8.16 (d, J=2.1 Hz, 1H), 7.90-7.98 (m, 2H), 7.45-7.53 (m, 2H), 7.22 (d, J=2.2 Hz, 1H), 3.71 (s, 3H), 3.01 (t, J=7.8 Hz, 2H), 2.71 (t, J=7.8 Hz, 2H), 1.51 (s, 9H).

Example 11. Transesterification of Benzotriazole Methyl Ester with Polyglycerol Polymer

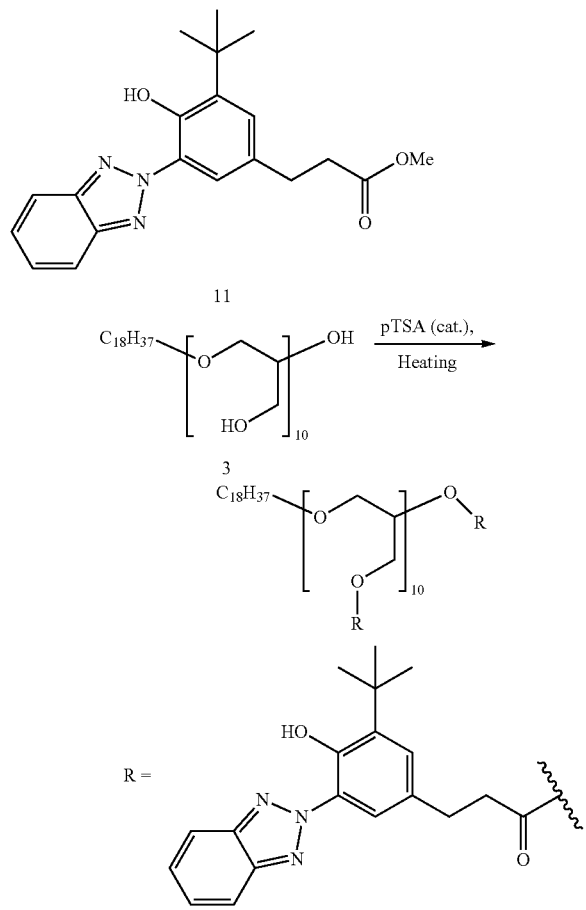

The transesterification of benzotriazole methyl ester 11 with polyglycerol 3 is illustrated in FORMULA XVII. A solution of polyglycerol 3 solution in MeOH was concentrated by rotary evaporation; residual solvent was removed overnight under vacuum at 75° C. Polyglycerol 3 (1.36 g, 14.9 hydroxyl milliequivalents) was added to a 100 mL 2-neck round bottom flask containing a magnetic stir bar. Benzotriazole methyl ester 11 (4.24 g, 12 mmol) and pTSA.H$_2$O (7.1 mg) was added to the flask. The flask was fitted with a nitrogen inlet adapter and distillation adapter with 100 mL receiving flask. The reaction flask was immersed in an oil bath, and the oil bath was warmed to 175° C. Within 20 minutes, all of the reactants had melted. The reaction mixture was stirred vigorously under a stream of nitrogen overnight. The following morning, the flask was placed under vacuum; residual UV-chromophore sublimed and collected in the distillation adapter. Heating under vacuum was continued overnight. The reaction mixture was then cooled to room temperature; the UV-absorbing polyglycerol product was obtained as a yellow, glassy solid. $^1$H NMR (400 MHz, CDCl$_3$) δ ppm 11.71 (br. s., 8H), 8.05 (br. s., 8H), 7.81 (br. s., 16H), 7.36 (br. s., 16H), 7.14 (br. s., 8H), 5.06-5.32 (br. s., 1H), 3.86-4.57 (m, 16H), 3.15-3.82 (m, 30H), 2.92 (br. s., 16H), 2.68 (br. s., 16H), 1.45 (br. s., 76H), 1.24 (br. s., 28H), 0.88 (t, J=6.6 Hz, 3H).

It can be seen from Examples 1-11 that analytical characterization of the resulting UV-absorbing polyethers was consistent with the expected structures. HPLC analysis of the polymers described in the examples provided evidence that the polymerization methods described resulted in low concentrations of residual UV absorbing monomer.

Example 12. Summary of SPF Results

Sun protection factor (SPF) measurements for UV absorbing polymers were performed using the following in vitro sun protection test method. Polymer samples were measured into 8 mL glass vials. Mixed $C_{12}$ to $C_{15}$ alkyl benzoates (a cosmetic oil solvent sold under the trade name FINSOLV TN by Innospec, Newark, N.J.) was added to the vial to achieve the desired weight percent solution of polymer. A magnetic stir bar was added to the vial, which was then sealed with a Teflon lined screw cap. The polymer/oil solution was stirred in a 100° C. aluminum reaction block until homogeneous. Once cooled, 32 mg of polymer solution was applied to a poly(methyl methacrylate) (PMMA) plate (a test substrate sold under the trade name HELIOPLATE HD6 by Helioscience, Marseille, France). The solution was spread evenly over the plate using one finger using a latex cot until the weight of sample on the plate had decreased to 26 mg. The baseline transmission was measured using an HD6 plate as received from the manufacturer. Absorbance was measured using a calibrated Labsphere UV-1000S UV transmission analyzer (Labsphere, North Sutton, N.H., USA). The absorbance measures were used to calculate SPF indices. SPF was calculated using methods known in the art. The equation used for calculation of SPF is described by Equation 1.

$$SPF_{in\ vitro}=[\int E(\lambda)I(\lambda)d\lambda]/[\int E(\lambda)I(\lambda)10^{-A_0(\lambda)}(d\lambda)] \quad (1)$$

where:
$E(\lambda)$=Erythema action spectrum
$I(\lambda)$=spectral irradiance received from the UV source
$A_0(\lambda)$=mean monochromatic absorbance of the test product layer before UV exposure
$d\lambda$=Wavelength step (1 nm)
and the integrations are each performed over the wavelength range from 290 nm to 400 nm.

Results of in vitro SPF testing of the polymers are reported in Examples 4, 7, and 9 as [wt. % in FINSOLV TN, mean SPF value] and are also shown in Table 1.

TABLE 1

| Polymer of example # | Polymer concentrations (wt %) | SPF | STDEV |
|---|---|---|---|
| 7 | 40 | 25 | |
| 4 | 40 | 32 | 11 |
| 9 | 40 | 31 | 8 |

It can be seen that the polymer compositions described were soluble in oils commonly used in topical cosmetic applications. Furthermore, it was demonstrated that solutions of polymers in these oils showed suitable SPF values using in vitro SPF test methods.

Composition Examples

The following example illustrates the low irritation of certain compositions of the present invention. Inventive compositions (E1-E3) include a polymer composition comprising a linear, ultraviolet radiation absorbing polyether that comprises a chemically bound UV-chromophore. The polymer composition was made consistent with the method described in Example 3B and Example 4. Inventive compositions (E1-E3) were prepared as shown in Table 2 and described below.

TABLE 2

|  | C1 | C2 | E1 | E2 | E3 | C3 |
|---|---|---|---|---|---|---|
| Water | 54.9 | 56.9 | 58.9 | 60.3 | 57.9 | 60.3 |
| Amigel | 0.3 | 0.3 | 0.3 | 0.3 | 0.3 | 0.3 |
| phenonip XB | 1 | 1 | 1 | 1 | 1 | 1 |
| Pemulen TR-2 | 0.3 | 0.3 | 0.3 | 0.3 | 0.3 | 0.3 |
| UV-Absorbing Polyether | 15 | 15 | 15 | 15 | 15 | 15 |
| Cetiol CC | 22.5 | 22.5 | 22.5 | 22.5 | 22.5 | 22.5 |
| Amphisol K | 6 | 4 | 2 | 0.6 | 3 |  |
| Emulsiphos* |  |  |  |  |  | 0.6 |

AMIGEL is sclerotium gum, available from Alban Muller International of Hialeah, Fla. PHENONIP XB is phenoxyethanol (and) methylparaben (and) ethylparaben (and) propylparaben, available from Clariant of Muttenz, Switzerland. PEMULEN TR-2 is Acrylates/C$_{10-30}$ Alkyl Acrylate Crosspolymer, available from Noveon/Lubrizol of Wickliffe, Ohio. CETIOL CC is Dicaprylyl Carbonate, available from Cognis, now BASF of Ludwigshafen, Germany. AMPHISOL K is a potassium cetyl phosphate (100% anionic), available from DSM of of Heerlen, Netherlands. EMULSIPHOS is potassium cetyl phosphate (*60% active anionic) and hydrogenated palm glycerides (40%) available from Symrise of Teterboro, N.J.

Inventive Examples E1-E3 and Comparative Examples C1-C3 were made by the following process. A water phase was prepared by adding water to a main vessel and heating to 80° C. with mixing. AMIGEL, PEMULEN TR2 and PHENONIP XB were added and mixed until dissolved. An oil phase was prepared by charging a vessel with CETIOL CC and mixing. At 60° C. UV-Absorbing Polyether was added. AMPHISOL K or EMULSIPHOS was added, and the mixture was heated to about 80° C. under mixing. The heated water phase was added to the oil phase with moderate shear. Moderate mixing was continued during cooling. In order to provide homogeneity, Examples E1-E3 and Comparative Example C3 were homogenized using a Silverson L4RT Homogenizer (Silverson Machines, East Longmeadow, Mass.).

The MODIFIED TEP values of Inventive Examples E1-E3 and Comparative Example C1-C3 were determined using the MODIFIED TEP as described above and the results reported in Table 3.

TABLE 3

| EXAMPLE | MODIFIED TEP VALUE |
|---|---|
| E1 | 0.095 |
| E2 | 0.19 |
| E3 | 0.16 |
| C1 | 0.51 |
| C2 | 0.37 |
| C3 | 0.42 |

The results of MODIFIED TEP testing indicate that the inventive examples have very low MODIFIED TEP values, which is indicative of surprisingly low irritation. In contrast, the comparative compositions C1 and C3, containing greater than about 3% anionic emulsifier, or less than about 0.5% anionic emulsifier have much greater MODIFIED TEP values.

It is understood that while the invention has been described in conjunction with the detailed description thereof, that the foregoing description is intended to illustrate and not limit the scope of the invention.

The invention claimed is:

1. A composition, comprising:
   a continuous water phase,
   a discontinuous oil phase homogeneously distributed in said water phase, said oil phase comprising a sunscreen agent comprising a polymer composition, said polymer composition comprising about 50% or more of a linear, ultraviolet radiation absorbing polyether that comprises a covalently bound UV-chromophore, wherein said polymer composition has a polydispersity index of about 1.5 or less; and
   an oil-in-water emulsifier component comprising an anionic oil-in-water emulsifier in an amount of about 0.5 percent to about 3 percent by weight of said composition;
   wherein said linear ultraviolet radiation absorbing polyether comprises a repeat unit selected from the group consisting of

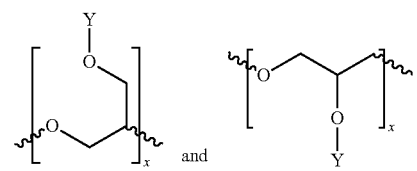

where Y is said covalently bound UV-chromophore.

2. The composition of claim 1, wherein said linear ultraviolet radiation absorbing polyether comprises a backbone having glyceryl repeat units.

3. The composition of claim 1, wherein said linear ultraviolet radiation absorbing polyether is characterized as having the structure:

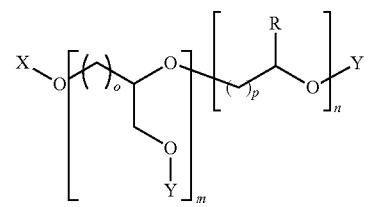

where R is a pendant group, Y represents said covalently bound UV-chromophore, X is a terminal group, and m and n are real numbers between 0 and 1.

4. The composition of claim 3, wherein m is 1 and n is 0.

5. The composition of claim 4, wherein X and R independently are selected from the group consisting of hydrogen, linear alkyl, alkenyl or alkynyl hydrocarbon chains, and linear siloxanes.

6. The composition of claim 1, wherein said UV-chromophore is selected from the group consisting of triazoles, camphors, dibenzoylmethanes, 4-aminobenzoic acid and alkane esters thereof, anthranilic acid and alkane esters thereof, salicylic acid and alkane esters thereof, hydroxycinnamic acid and alkane esters thereof, dihydroxy-, dicarboxy-, and hydroxycarboxybenzophenones and alkane ester or acid halide derivatives thereof, dihydroxy-, dicarboxy-, and hydroxycarboxychalcones and alkane ester or acid halide derivatives thereof, dihydroxy-, dicarboxy-, and hydroxycarboxycoumarins and alkane ester or acid halide derivatives thereof, benzalmalonate, benzimidazole derivatives, benzoxazole derivatives, 3-(3-(2H-benzo[d][1,2,3]triazol-2-yl)-5-(tert-butyl)-4-hydroxyphenyl), 6-octyl-2-(4-(4,6-di([1,1'-biphenyl]-4-yl)-1,3,5-triazin-2-yl)-3-hydroxyphenoxy)propanoate and trioctyl 2,2',2''-(((1,3,5-triazine-2,4,6-triyl) tris(3-hydroxybenzene-4,1-diyl))tris(oxy)) tripropanoate.

7. The composition of claim 1, wherein said UV-chromophore is selected from the group consisting of a benzotriazole and a triazine.

* * * * *